US011732242B2

(12) United States Patent
Noggle et al.

(10) Patent No.: US 11,732,242 B2
(45) Date of Patent: *Aug. 22, 2023

(54) AUTOMATED SYSTEM FOR PRODUCING INDUCED PLURIPOTENT STEM CELLS OR DIFFERENTIATED CELLS

(71) Applicant: New York Stem Cell Foundation, Inc., New York, NY (US)

(72) Inventors: Scott Noggle, New York, NY (US); Kevin C. Eggan, Boston, MA (US); Stephen Chang, Poway, CA (US); Susan L. Solomon, New York, NY (US)

(73) Assignee: New York Stem Cell Foundation, Inc., New York, NY (US)

( * ) Notice: Subject to any disclaimer, the term of this patent is extended or adjusted under 35 U.S.C. 154(b) by 209 days.

This patent is subject to a terminal disclaimer.

(21) Appl. No.: 17/194,047

(22) Filed: Mar. 5, 2021

(65) Prior Publication Data
US 2021/0332330 A1 Oct. 28, 2021

Related U.S. Application Data

(63) Continuation of application No. 16/398,117, filed on Apr. 29, 2019, now Pat. No. 10,968,435, which is a
(Continued)

(51) Int. Cl.
*C12N 5/074* (2010.01)
*C12M 1/12* (2006.01)
(Continued)

(52) U.S. Cl.
CPC ............ *C12N 5/0696* (2013.01); *C12M 23/04* (2013.01); *C12M 35/02* (2013.01); *C12M 35/08* (2013.01); *C12M 47/04* (2013.01)

(58) Field of Classification Search
CPC .. C12N 5/0696; C12N 5/0606; C12N 5/0647; C12N 5/069; C12N 2500/02;
(Continued)

(56) References Cited

U.S. PATENT DOCUMENTS 7,879,601 B2   2/2011   Smith et al.
8,211,697 B2   7/2012   Sakurada et al.
(Continued)

FOREIGN PATENT DOCUMENTS

EP   2423302 A1   2/2012
EP   2481795 A1   8/2012
(Continued)

OTHER PUBLICATIONS

Aasen, T. et al., "Efficient and rapid generation of induced pluripotent setm cells from human keratinocytes", Nature Biotechnology, vol. 26, No. 11, Nov. 1, 2008, pp. 1276-1284.
(Continued)

*Primary Examiner* — William H. Beisner
*Assistant Examiner* — Danielle B Henkel
(74) *Attorney, Agent, or Firm* — Goodwin Procter LLP

(57) ABSTRACT

The invention provides an automated system for producing induced pluripotent stem cells (iPSCs) from adult somatic cells. Further, the system is used for producing differentiated adult cells from stem cells.

9 Claims, 15 Drawing Sheets

Related U.S. Application Data continuation of application No. 13/691,258, filed on Nov. 30, 2012, now Pat. No. 10,273,459.

(60) Provisional application No. 61/700,792, filed on Sep. 13, 2012, provisional application No. 61/580,007, filed on Dec. 23, 2011, provisional application No. 61/565,818, filed on Dec. 1, 2011.

(51) Int. Cl.
  *C12M 1/42* (2006.01)
  *C12M 1/00* (2006.01)

(58) Field of Classification Search
  CPC .......... C12N 2500/90; C12N 2501/155; C12N 2501/165; C12N 2501/70; C12N 2506/02; C12N 2501/115; C12M 47/04; C12M 35/02; C12M 35/08; C12M 23/04
  See application file for complete search history.

(56) References Cited

U.S. PATENT DOCUMENTS

| | | | |
|---|---|---|---|
| 10,273,459 B2* | 4/2019 | Noggle | C12M 35/08 |
| 10,968,435 B2* | 4/2021 | Noggle | C12M 47/04 |
| 2001/0051374 A1 | 12/2001 | Mclaughlin-Taylor et al. | |
| 2006/0179502 A1 | 8/2006 | Kauselmann et al. | |
| 2007/0238175 A1 | 10/2007 | Chi | |
| 2009/0029462 A1* | 1/2009 | Beardsley | C12N 5/0606 |
| | | | 435/303.1 |
| 2010/0167300 A1 | 7/2010 | Esmaeli-Azad | |
| 2010/0216181 A1 | 8/2010 | Daigh et al. | |
| 2010/0279403 A1 | 11/2010 | Rajesh et al. | |
| 2011/0020814 A1* | 1/2011 | Dimos | C12N 5/0696 |
| | | | 435/325 |
| 2011/0171185 A1* | 7/2011 | Klimanskaya | C12N 5/0696 |
| | | | 424/93.21 |
| 2011/0200568 A1 | 8/2011 | Ikeda et al. | |
| 2011/0286978 A1* | 11/2011 | Klimanskaya | C12N 5/0696 |
| | | | 435/441 |
| 2011/0306516 A1 | 12/2011 | Kahler et al. | |
| 2012/0135525 A1* | 5/2012 | Brown | C12N 5/0696 |
| | | | 435/377 |
| 2013/0345094 A1 | 12/2013 | Noggle et al. | |
| 2014/0220681 A1 | 8/2014 | Valamehr et al. | |

FOREIGN PATENT DOCUMENTS

| | | |
|---|---|---|
| JP | 2005-531300 A | 10/2005 |
| JP | 2010-532173 A | 10/2010 |
| KR | 10-2010-0059789 A | 6/2010 |
| KR | 10-2011-0094348 A | 8/2011 |
| WO | WO-2003/087292 A2 | 10/2003 |
| WO | WO-2008/107695 A1 | 9/2008 |
| WO | WO-2009/006422 A1 | 1/2009 |
| WO | WO-2010/077955 A1 | 7/2010 |
| WO | WO-2011/026222 A1 | 3/2011 |
| WO | WO-2013/082509 A1 | 6/2013 |

OTHER PUBLICATIONS

Abyzov, A. et. al., "Somatic copy number mosaicism in human skin revealed by induced pluripotent stem cells", Nature, vol. 492, 2012, pp. 438-442.
Anonymous, "081-09.04.10: NRW-Konsortium baut "StemCellFactory"", UKB Universitätsklinikum BONN / Medizinische Fakultät, (Apr. 9, 2010), URL: https://www.ukb.uni-bonn.de/42256BC8002AF3E7/vwWebPagesByID/E48E477507DEDBB9C12577000030729D<https://protect-us.mimecast.com/s/i000C319Yvfg7zv4HggKLY?domain=ukb.uni-bonn.de>, (Mar. 16, 2015).
Beers, J. et. al., "A cost-effective and efficient reprogramming platform for large-scale production of integration-free human induced pluripotent stem cells in chemically defined culture", Sci. Rep. 5, 11319 (2015).
Bock, C. et al., "Refernce maps of human ES and iPS cell variation enable high-throughput characterization of pluripotent cell lines", Cell 144, pp. 439-452 (2011).
Byrne, S.M. et al., "Genome editing in human stem cells", Methods in Enzymology, 2014, vol. 546, pp. 119-138.
Cahan, P. et. al., "Origins and implications of pluripotent stem cell variability and heterogeneity", Nat. Rev. Mol. Cell Biol. 14, pp. 357-368 (2013).
Carey, B.W. et. al., "Reprogramming factor stoichiometry influences the epigenetic state and bilogical properties of induced pluripotent stem cells", Cell Stem Cell 9, pp. 588-598 (2011).
Chen, K.G. et. al., "Human pluripotent stem cell culture: considerations for maintenance, expansion, and therapeutics", Cell Stem Cell 14, pp. 13-26 (2014).
Cheng, L. et. al., "Low incidence of DNA sequence variation in human induced pluripotent stem cells generated by nonintegrating plasmid expression", Stem Cell 10, pp. 337-344 (2012).
Colman, A. et. al., "Pluripotent stem cells and disease modeling", Cell Stem Cell 5, pp. 244-247 (2009).
Conway, M.K. et. al., "Scalable 96-well plate based iPSC culture and production using a robotic liquid handling system", J. Vis. Exp. 99, e52755 (2015).
Douvaras, P. et. al., "Efficient generation of myelinating oligodendrocytes from primary progressive multiple sclerosis patients by induced pluripotent stem cells", Stem Cell Reports, vol. 3, 2014, pp. 250-259.
Fusaki, N. et. al., "Efficient induction of transgene-free human pluripotent stem cells using a vector based on Sendaivirus, an RNA virus that does not integrate into the host genome", Proc. Jpn. Acad., Ser. B, Phys. Biol. Sci. 85, pp. 348-362 (2009).
Hanna, J. et. al., "Direct cell reprogramming is a stochastic process amenable to acceleration", Nature 462, pp. 595-601 (2009).
Hannan, N.R.F. et. al., "Production of hepatocyte-like cells from human pluripotent stem cells", Nat. Protoc. 8, pp. 430-437 (2013).
Harris, P. et. al., "Research electronic data capture (REDCap)—a metadata-driven methodology and workflow process for providing translational research informatics support", J. Biomed. Inform. 42, pp. 377-381 (2009).
Haupt, S. et. al., "Automated selection and harvesting of pluripotent stem cell colonies", Biotechnology and applied Biochemistry, vol. 59, No. 2, Mar. 1, 2012, pp. 77-87.
Heintze, J. et. al., "A CRISPR CASe for high-throughput silencing", Frinteirs in Genetics, Oct. 2013, vol. 4, Article 193, pp. 1-6.
International Preliminary Report on Patentability received for PCT Patent Application No. PCT/US12/67417, dated Jun. 12, 2014, 9 pages.
International Preliminary Report on Patentability received for PCT Patent Application No. PCT/US14/44702, dated Dec. 29, 2015, 7 pages.
International Search and Written Opinion received for PCT Patent Application No. PCT/US14/44702, dated Nov. 6, 2014, 10 pages.
International Search Report and Written Opinion received for PCT Patent Application No. PCT/US12/67417, dated Apr. 22, 2013, 12 pages.
International Search report dated May 19, 2016, regarding PCT/US2015/000498, 12 pages.
Joannides, A. et al., "Automated mechanical passaging: a novel and efficient method for human embryonic stem cell expansion", Stem Cells. (2006), vol. 24, No. 2, pp. 230-235.
Kahler, D.J. et al., "Improved methods for reprogramming human dermal fibroblasts using fluorescence activated cell sorting", PLoS ONE 8, e59867 (2013).
Kajiwara, M. et al., "Donor-dependent variations in heptic differentiation from human-induced pluripotent stem cells", Proc. Natl. Acad. Sci. USA 109, pp. 12538-12543 (2012).
Kami, D. et al., "Large-scale cell production of stem cells for clinical application using the automated cell processing machine", BMC Biotechnology, 13:102, Nov. 15, 2013, 9 pages.
Lane, L. "Simplify and Accelerate your Cell Separation with Automation", Biocompare, available online at <https://www.

(56) References Cited

OTHER PUBLICATIONS biocompare.com/editorial-articles/140610-automated-cell-separation-a-painless-procedure/>, Jul. 3, 2013, pp. 1-3.
Li, C. et al., "Genetic heterogeneity of induced pluripotent stem cells: results from 24 clones derived from a single C57BL/6 mouse", PLoS ONE 10, e0120585 (2015).
Lian, X. et al., "Directed cardiomyocyte differentiation from human pluripotent stem cells by modulatting Wnt/f3-catenin signaling under fully defined conditions", Nat. Protoc. 8, pp. 162-175 (2013).
Liang, G. et al., "Genetic and epigenetic variations in iPSCs: potential causes and implications for application", Cell Stem Cell 13, pp. 149-159 (2013).
Martincorena, I. et al., "Tumor evolution. High burden and pervasive positiveselection of somatic mutations in normal human skin", Science (New York, N.Y.) 348, pp. 880-886 (2015).
Mayshar, Y. et al., "Identification and classification of chromosomal aberrations in human induced pluripotent stem cells", Cell Stem Cell 7, pp. 521-531 (2010).
McKernan, R. et al., "What is the point of large-scale collections of human induced pluripotent stem cells?" Nat. Biotechnol. 31, pp. 875-877 (2013).
Mekhoubad, S. et al., "Erosion of dosage compensation impacts human iPSC disease modeling", Cell Stem Cell 10, pp. 595-609 (2012).
Morris, A.P. et al., Large-scale association analysis provides insights into the genetic architecture and pathophysiology of type 2 diabetes, Nat. Genet. 44, pp. 981-990 (2012).
Paull, D. et al., "Automated, high-throughput derivation, characterization and differentiation of induced pluripotent stem cells", Nature Methods, vol. 12, No. 9, Sep. 2015, pp. 885-892.
Phang, R. et al., "Zinc finger nuclease-expressing baculoviral mediate targeted genome integration of reprogramming factor genes to facilitate the generation of human induced pluripotent stem cells", Stem Cells Translational Medicine: SCTM, vol. 2, No. 12, Oct. 28, 2013, pp. 935-945.
R Development Core Team: "R: A language and environmental for statistical computing" (R Foundation for Statisitical Computing, 2015).
Ramalingam, S. et al., "Generation and Genetic engineering of human induced pluripotent stem cells using designed zinc finger nucleases" Stem Cell and Development, 2013, vol. 22, No. 4, pp. 595-610.
Robinton, D.A. et al., "The promise of induced pluripotent stem cells in research and therapy", Nature 481, pp. 295-305 (2012).
Rohani, L. et al., "The aging signature: a hallmark of induced pluripotent stem cells?" Aging Cell 13, pp. 2-7 (2014).
Santostefano, K.E. et al., "A practical guide to induced pluripotent stem cell research using patient samples", Lab. Invest. 95, pp. 4-13 (2015).
Taguchi, A. et al., "Redfining the in vivo origin of metanephric nephron progenitors enables generation of complex kidney structures from pluripotent stem cells" Cell Stem Cell 14, pp. 53-67 (2014).
Takahashi, K. et al., "Induction of pluripotent stem cells from adult human fibroblasts by defined factors" Cell 131, pp. 861-872 (2007).
Techan Cellerity (TM) documents published by Techan 2008-2009, pp. 1-18.
Terstegge, S. et al., "Automated maintenance of embryonic stem cell cultures" Biotechnol. Bioeng. 96, pp. 195-201 (2007).
Thomas, R. et al., "Automated, scalable culture of human embryonic stem cells in feeder-free conditions", Biotechnol. Bioeng. 102, pp. 1636-1644 (2009).
Tyson, C. et al., "Expansion of a 12-kb VNTR containing the REXO1L1 gene cluster underlies the microscopically visible euchromatic variant of 8q21.2", Eur. J. Hum. Gent. 22, pp. 458-463 (2014).
Utikal, J. et al., "Immortalization eliminates a roadblock during cellular reprogramming into iPS cells", Nature 460, pp. 1145-1148 (2009).
Valamehr, B. et al. "A novel platform to enable the high-throughput derivation and characterization of feeder-free human iPSCs", Sci. Rep. 2, 213 (2012).
Vallot, C. et al., "Erosion of X chromosome inactivation in human pluripotent cells initiates with XACT coatingand depends on a specific heterochromatin landscape", Cell Stem Cell 16, pp. 533-546 (2015).
Wagner, K. et al., "Cryopreserving and recovering of human iPS cells using complete knockout serum replacement feeder-free medium", J. Visual Experiments, 2010, pp. 1-3.
Warren, L. et al., "Feeder-free derivation of human induced pluripotent stem cells with messengar RNA", Sci. Rep. 2, 657 (2012).
Warren, L. et al., "Highly efficient reprogramming to pluripotent and directed differentiation of human cells with synthetic modified mRNA", Cell Stem Cell 7, pp. 618-630 (2010).
Watanabe, K. et al., "A ROCK inhibitor permits survival of dissociated human embryonic stem cells" Nat. Biotechnol. 25, pp. 681-686 (2007).
Woodard, C.M. et al., "iPSC-derived dopamine neurons reveal differences between monozygotic twins discordant for Parkinson's disease", Cell Reports 9, pp. 1173-1182 (2014).
Zhou, H. et al., "Rapid and efficient generation of transgene-free iPSC from a small volume of cryopreserved blood", Stem Cell Rev. 11, pp. 652-665 (2015).

* cited by examiner

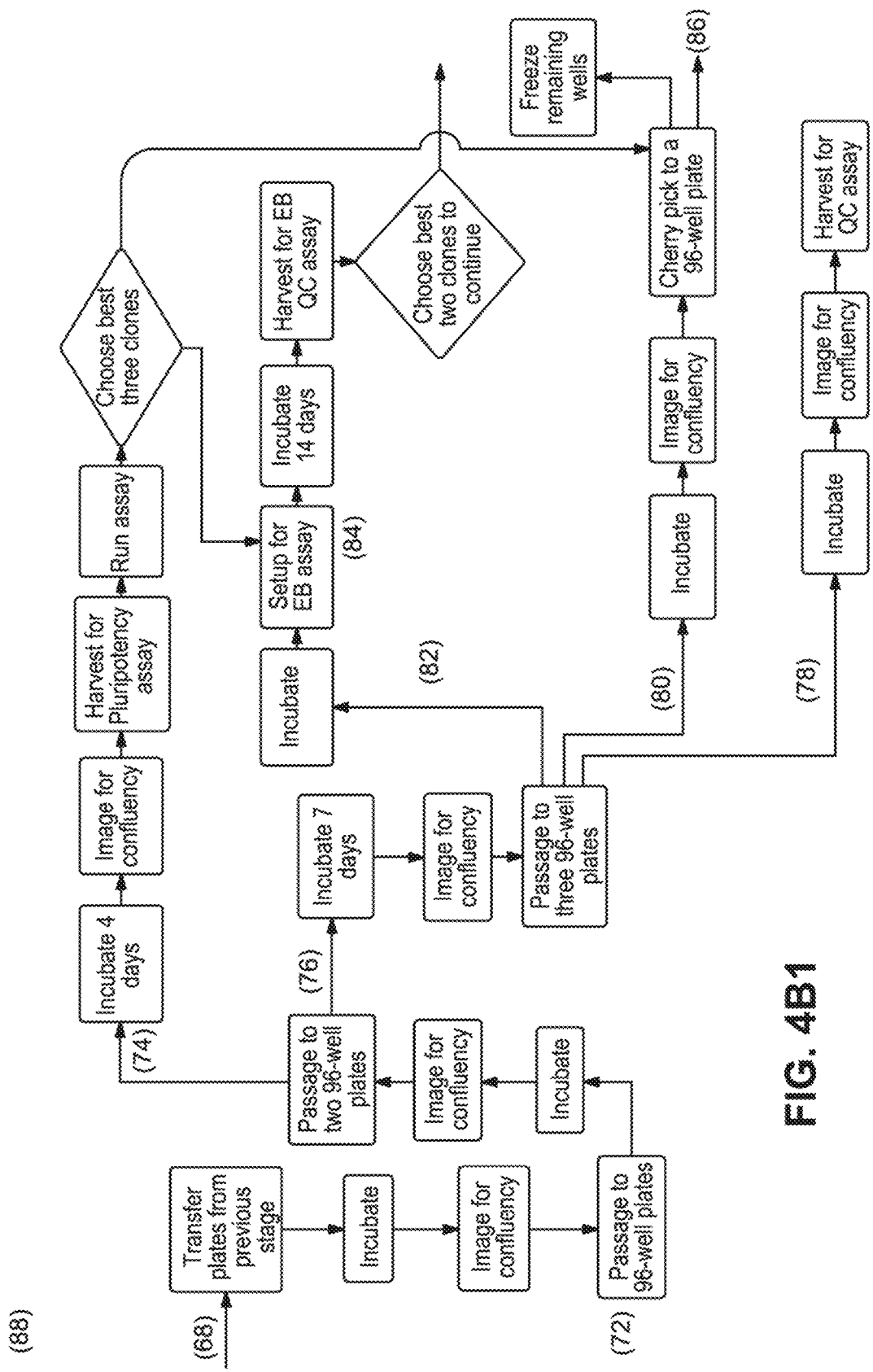
FIG. 4B1

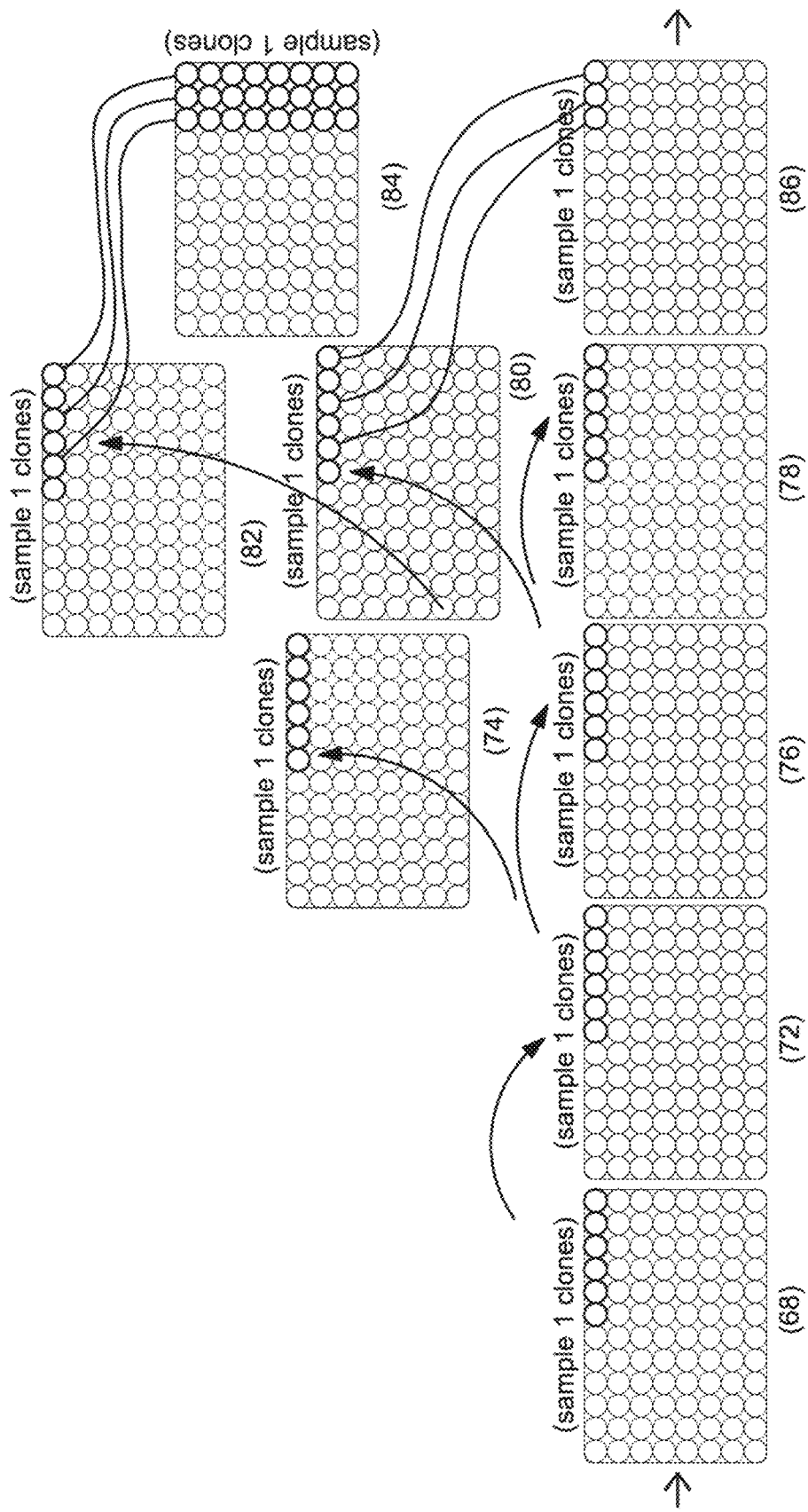
FIG. 4B2

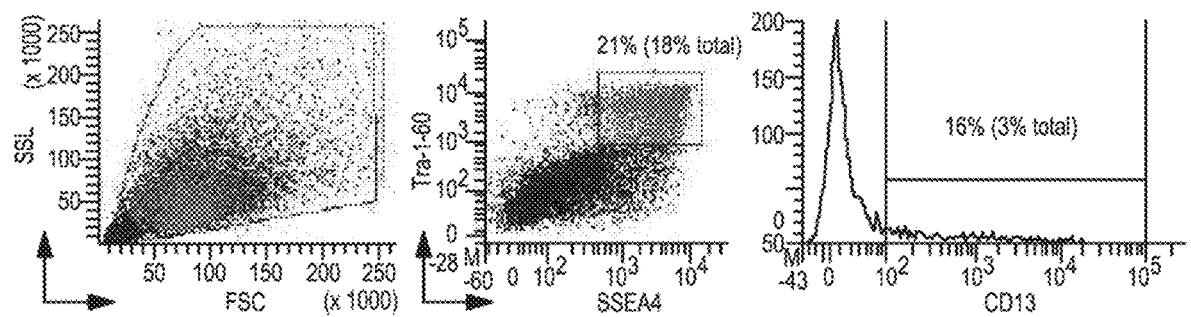
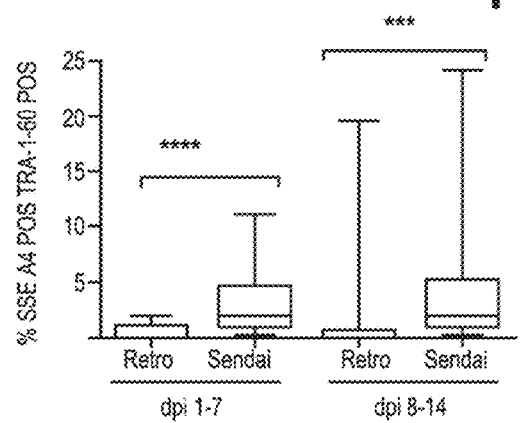
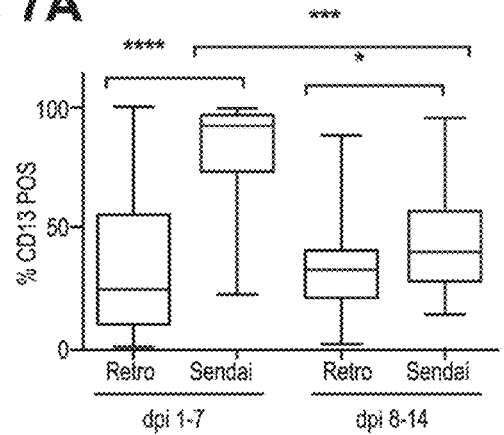
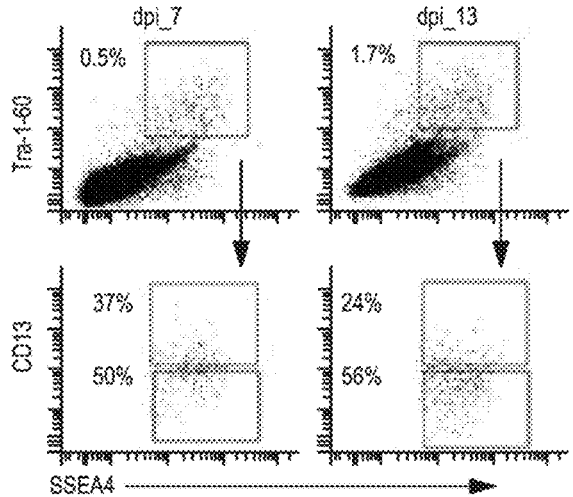
FIG. 7A
FIG. 7B
FIG. 7C
FIG. 7D

AUTOMATED SYSTEM FOR PRODUCING INDUCED PLURIPOTENT STEM CELLS OR DIFFERENTIATED CELLS

CROSS-REFERENCE TO RELATED APPLICATIONS

This application is a continuation application of U.S. application Ser. No. 16/398,117 filed Apr. 29, 2019, now U.S. Pat. No. 10,968,435, issued on Apr. 6, 2021; which is a continuation application of U.S. application Ser. No. 13/691,258 filed Nov. 30, 2012, now U.S. Pat. No. 10,273,459; issued on Apr. 30,2019; which claims the benefit under 35 USC § 119(e) to U.S. Application Ser. No. 61/700,792 filed Sep. 13, 2012, U.S. Application Ser. No. 61/580,007 filed Dec. 23, 2011, and to U.S. Application Ser. No. 61/565,818 filed Dec. 1, 2011, all now expired. The disclosure of each of the prior applications is considered part of and is incorporated by reference in the disclosure of this application.

BACKGROUND OF THE INVENTION

Field of the Invention

The present invention relates generally to an automated system for producing induced pluripotent stem cells (iPSC) from differentiated adult cells and more specifically to an automated system for isolating somatic cells from tissue samples, producing iPSC lines from adult differentiated cells by reprogramming such cells, identifying the pluripotent reprogrammed adult cells among other cells, and expanding the identified reprogrammed cells.

Background of the Invention

Stem cells are unspecialized cells that self-renew for long periods through cell division, and can be induced to differentiate into cells with specialized functions, i.e., differentiated cells. These qualities give stem cells great promise for use in therapeutic applications to replace damaged cells and tissue in various medical conditions. Embryonic stem (ES) cells are derived from the blastocyst of an early stage embryo and have the potential to develop into endoderm, ectoderm, and mesoderm (the three germ layers) (i.e., they are "pluripotent"). In vitro, ES cells tend to spontaneously differentiate into various types of tissues, and the control of their direction of differentiation can be challenging. There are unresolved ethical concerns that are associated with the destruction of embryos in order to harvest human ES cells. These problems limit their availability for research and therapeutic applications.

Adult stem (AS) cells are found among differentiated tissues. Stem cells obtained from adult tissues typically have the potential to form a more limited spectrum of cells (i.e., "multipotent"), and typically only differentiate into the cell types of the tissues in which they are found, though recent reports have shown some plasticity in certain types of AS cells. They also generally have a limited proliferation potential.

Induced pluripotent stem cells (iPSC or iPSCs) are produced by laboratory methods from differentiated adult cells. iPSCs are widely recognized as important tools, e.g., for conducting medical research. Heretofore, the technology for producing iPSCs has been time-consuming and labor-intensive. Differentiated adult cells, e.g., fibroblasts, are reprogrammed, cultured, and allowed to form individual colonies which represent unique clones. Previously, identifying these types of cells has been difficult because the majority of the cells are not fully-reprogrammed iPSC clones. The standard is for iPSC clones to be selected based on the morphology of the cells, with desirable colonies possessing sharply demarcated borders containing cells with a high nuclear-to-cytoplasmic ratio. When clones are identified, they are manually-picked by micro-thin glass tools and cultured on "feeder" layers of cells typically, Murine Embryonic Fibroblasts (MEF). This step is performed typically at 14-21 days post-infection with a reprograming vector. Then the clones are expanded for another 14-21 days or more, prior to undergoing molecular characterization.

Others have focused on developing techniques to rapidly and more accurately identify and characterize fully-reprogrammed adult fibroblasts and their downstream differentiation potential (Bock et al., 2011, *Cell* 144: 439-452; Boulting et al., 2011, Nat Biotechnol 29: 279-286). Also see, for example, co-owned U.S. Ser. No. 13/159,030, filed on Jun. 13, 2011, describing the use of Fluorescence Activated Cell Sorting (FACS) to identify and live sort unique subpopulations of s as defined by unique expression patterns of surface proteins.

Thus, stem cells are an attractive source of cells for therapeutic applications, medical research, pharmaceutical testing, and the like. However, there remains a longstanding need in the art for an automated system for rapidly producing and isolating reproducible iPSC cell lines under standard conditions in order to meet these and other needs.

SUMMARY OF THE INVENTION

The invention provides a system for using somatic cells from adult tissue and producing induced pluripotent stem cells (iPSCs) from those somatic cells, e.g., adult fibroblasts. In one aspect, the system also utilizes previously isolated somatic cells as a starting point.

The invention provides an automated system for generating and isolating iPSCs, comprising:
  a somatic cell plating unit for placing somatic cells on a plate; and
  an induction unit for automated reprogramming of the somatic cells by contacting the somatic cells on the somatic cell plating unit with reprogramming factors to produce iPSCs. In one embodiment, the system further comprises a sorting unit for selectively sorting and isolating the iPSCs produced by the induction unit, e.g., by identifying iPSC specific markers, including, e.g., surface markers on the cells. In one illustrative example, the somatic cells are fibroblasts.

Further, in one aspect, the invention provides an automated system for generating and isolating differentiated adult cells from stem cells, e.g., embryonic stem (ES) cells or mesenchymal stem (MS) cells, comprising:
  a stem cell plating unit for placing stem cells on a plate; and
  an induction unit for automated reprogramming of stem cells by contacting the cells on the stem cell plating unit with reprogramming factors to produce differentiated adult cells. In one embodiment, the system further comprises a sorting unit for selectively sorting and isolating the differentiated adult cells produced by the induction unit.

In one aspect, the invention provides an automated system for generating and isolating differentiated adult cells from induced pluripotent stem cells (iPSC), comprising:

an iPSC plating unit for placing iPSCs on a plate; and
an induction unit for automated reprogramming of iPSCs by contacting the iPSCs on the iPSC plating unit with reprogramming factors to produce differentiated adult cells. In a further aspect, the system includes a sorting unit for selectively sorting and isolating the differentiated adult cells produced by the induction unit by identifying markers specific to differentiated adult cells.

The invention also provides iPSCs, differentiated or transdifferentiated cells produced using the system of the invention. Further, an array comprising a population of cells obtained from invention iPSCs or differentiated cells are included herein. For example, the differentiated cells include hematopoetic stem cells, muscle cells, cardiac muscle cells, liver cells, cartilage cells, epithelial cells, urinary tract cells, and neuronal cells. In another aspect, a cell bank generated by the invention system is included.

BRIEF DESCRIPTION OF THE DRAWINGS

FIGS. 4A-4C show examples of a flow of patient samples through multi-well tissue culture plates during an automated reprogramming process.

In FIG. 6A, biopsies or discarded tissue are plated in multiple wells of a 6-well dish and maintained by an automated system that feeds, images, passages, and freezes fibroblast outgrowths. Examples of the image analysis interface are shown for a typical sample.

FIG. 6B: Cell numbers are extrapolated from confluence measurements based on linear regression from a standard curve generated independently. FIG. 6C: An example of cell counts for a typical biopsy outgrowth maintained on our automated system. Extrapolated cell numbers per patient sample are plotted for each well independently (top) allowing calculation of total output from the sample (bottom).

FIGS. 7A-7D show FACS analyses and graphs showing automated iPSC reprogramming. Expression levels of pluripotent surface markers on reprogrammed human fibroblasts were followed over a 3 week period to observe reprogramming kinetics and determine optimal time points at which to isolate defined cell populations. FIG. 7A FACS gating scheme used for analysis. FIG. 7B: A substantial proportion of cells co-expressing traditional pluripotency surface markers SSEA4 & TRA-1-60 retain the fibroblast marker CD13 at all time points during reprogramming using viral vectors to introduce reprogramming factors such as Oct4, Sox2, Klf4 and c-Myc. Box plots indicating aggregated data from 131 experiments (Retrovirus, n=66, Sendai virus, n=65) are shown. While Sendai mediated reprogramming produces more SSEA4/TRA-1-60 double positive cells (FIG. 7C), there is a delay in elimination of CD13 from the surface. (FIG. 7D) Example staining pattern of a patient cell line reprogrammed using Sendai/Cytotune system on our automated system. At both 7 and 13 days post infection (dpi), more than half of SSEA4/TRA-1-60 double positive cells have lost CD13. Additionally, at both time points assayed, CD13 negative/Nanog positive cells are present in this fraction, suggesting these can be isolated by negative selection against CD13.

FIG. 8A shows Non-reprogrammed cell populations can be depleted from cultures of iPSCs by negative selection by a fibroblast marker. In the example, fibroblasts are efficiently removed from the culture containing 2% established iPSCs leaving TRA-1-60 positive iPSCs untouched. FIG. 8B shows a Miltenyi MultiMACS system integrated into Hamilton liquid handler that can sort 24 samples in parallel. FIG. 8C is an illustration of the iPSC-enriched fraction from the anti-fibroblast magnetic negative selection step that is plated on 96-well imaging plates at limiting dilution. These plates are screened using live-cell staining for the pluripotency surface marker TRA-1-60 or TRA-1-81. Wells with TRA-1-60 positive iPSCs are identified by automated image analysis using the Celigo software capable of single colony confirmation. Wells that meet both criteria of containing a single colony that is positive for the surface marker are selected for passaging, expansion, and QC.

FIG. 9A shows transcript counts after normalization to HK gene expression for two human ESC lines, Sendai positive control, fibroblast negative control, and iPSC lines derived by FACS sorting assayed at passage 5 and 10. All assays are run relative to a panel of normal human ESC and iPSC lines maintained under similar conditions. FIG. 9B illustrates the second stage of our quality control screen, which uses an additional 83 germ layer/lineage markers to monitor differentiation capability in embryoid body assays. Single EBs are generated and pooled to collect RNA for expression analysis of germ layer markers in the embryoid body scorecard assay. Shown is a cluster dendrogram analysis of gene expression in EBs collected from nine different embryonic stem cells lines After normalization, data generated from direct lysis of six EBs compares favorably to data generated from total RNA extracted and purified from EBs prepared from bulk culture.

FIG. 10A is an example of the nCounter Karyotype assay on BC1 iPSCs; FIG. 10B is an example of the nCounter Karyotype assay on 1016 fibroblasts with partial gain and loss of chromosome arms. Comparison to Affymetrix SNP 6.0 chip data demonstrating copy number gains on a portion of the q arm of Chr1 (top track, 1q21.2-1q43) and loss of part of the long arm of Chr6 (bottom track, 6q16.3-6q26).

DETAILED DESCRIPTION OF THE PREFERRED EMBODIMENT

Figure 1:
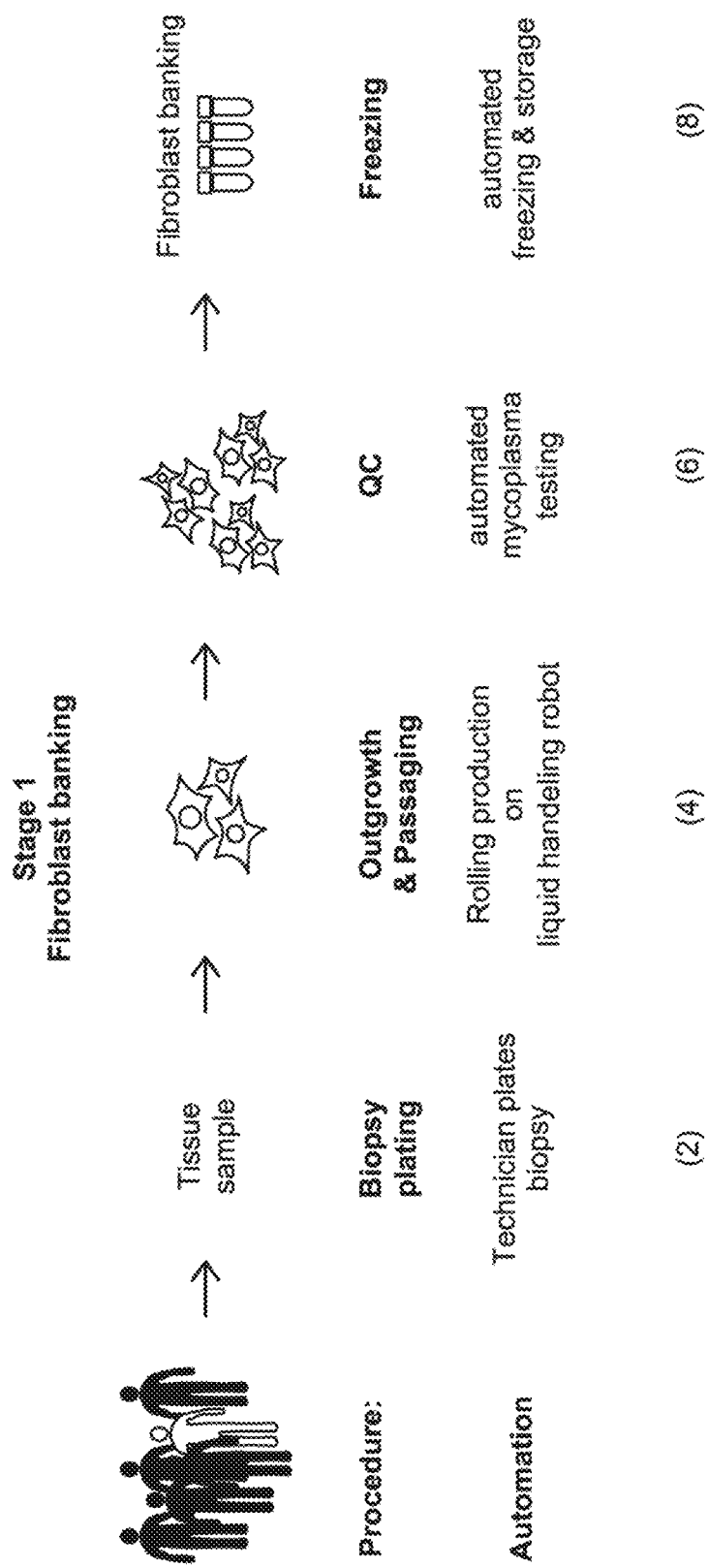
FIG. 1 shows steps for acquiring a fibroblast cell bank.

The present invention is based on the generation of an automated system for producing iPSCs and differentiated cells. The invention system greatly improves the efficiency and reproducibility of making standardized iPSC lines. Typically, researchers generate iPSCs by hand, which limits the cells utility due to researcher variability and an inability to generate large numbers of cells. The invention system circumvents these problems with a completely automated system from receipt of the tissue sample to banking of large stocks of well-defined iPSC lines. The system allows for generation of large numbers of cells from many donors, which will facilitate the use of iPSC technology to discover treatments and cures for many diseases.

In one embodiment, the workflow system of the invention includes an automated system for generating and isolating iPSCs, comprising:
 a somatic cell, e.g., fibroblast, plating unit for placing cells on a plate; and
 an induction unit for automated reprogramming of cells by contacting the cells on the plating unit with reprogramming factors to produce iPSCs. In a further embodiment, the invention system includes a sorting unit for selectively sorting and isolating the iPSCs produced by the induction unit by identifying iPSC specific markers, including, e.g., surface markers or green fluorescent proteins inserted by a transfection vector.

In another embodiment, the invention provides an automated system for generating and isolating differentiated adult cells from stem cells, e.g., embryonic stem (ES) cells or mesenchymal stem (MS) cells, comprising:
 a stem cell plating unit for placing cells, e.g., ES or MS cells, on a plate; and
 an induction unit for automated reprogramming of cells by contacting the cells on the stem cell plating unit with reprogramming factors to produce differentiated adult cells. In one embodiment, the system further includes a sorting unit for selectively sorting and isolating the differentiated adult cells produced by the induction unit by identifying markers specific to the differentiated adult cells.

In yet another embodiment, the invention provides an automated system for generating and isolating differentiated adult cells from induced pluripotent stem cells (iPSCs), comprising:
 an iPSC plating unit for placing iPSCs on a plate; and
 an induction unit for automated reprogramming of iPSCs by contacting the iPSCs on the iPSC plating unit with reprogramming factors to produce differentiated adult cells. In one embodiment, the system further includes a sorting unit for selectively sorting and isolating the differentiated adult cells produced by the induction unit by identifying markers specific to the differentiated adult cells.

The invention provides an automated workflow system for producing iPSCs from differentiated adult cells. Broadly, the inventive workflow system provides a new workflow system that starts with adult differentiated cells and results in either iPSCs or adult cells derived from pluripotent cells. In one embodiment, the adult differentiated cells are preferably fibroblasts obtained, e.g., from skin biopsies. The adult fibroblasts are converted into induced pluripotent stem cells (iPSCs) by the inventive workflow that incorporates automation and robotics. The inventive workflow system is capable of generating thousands of iPSCs in parallel resulting in an accelerated timeframe, in a period of months instead of the years, which would have previously been required. The inventive workflow system can be adapted to any cell isolation system for starting material and be applied to direct or indirect reprogramming and transdifferentiation, for example. The inventive workflow system will allow production employing cellular arrays of cells from 6, 24, 96, 384, 1536 sized arrays, or greater. The inventive workflow system is flexible and will allow for multiple iterations and flexibility in cell type and tissue.

The Workflow System

The workflow system is broken down into four independently-operated units:
 (1) Quarantine Somatic Cell Isolation and Growth (System 1);
 (2) Quarantine Assay (System 2);
 (3) Thawing, Infection and Identification (Systems 3, 4, and 5); and
 (4) Maintenance, QC, Expansion, and Freezing (Systems 6, 7, and 8)

Additionally, an automated −80 storage and retrieval system for storing fibroblasts and final clones in 1.4 mL Matrix screw cap tubes, is part of the system. The systems, and the steps and operations that each unit will perform, will be described below.

System 1, Part A: Quarantine Somatic Cell Isolation and Growth Workflow, Biopsy Processing Pre-*Mycoplasma* Test
 1. Technician will plate 40 biopsies per week in 6-well dishes;
 2. 6-well plates will be maintained in quarantine incubator with 200-plate capacity;
 3. Periodic confluency checks are performed on an integrated Cyntellect Celigo Cytometer.

The system components that may be used to perform these automated steps include by way of example, STARlet Manual Load, a Modular Arm for 4/8/12 ch./MPH, 8 channels with 1000 μl Pipetting Channels and an iSWAP Plate Handler, all available from Hamilton Science Robotics. If centerfuging is needed or desired, an Agilent VSpin Microplate Centerfuge can be used. The software may be Celigo API Software. The incubator may be a Cytomat Incubator. For plate handling a Cytomat 24 Barcode Reader, Cytomat 23 mm Stackers, and a Cytomat 400 mm transfer station may be used. For plate tilting, one may use a MultiFlex Tilt Module. The system controller may be a Dell PG with a Windows XP operating system. The carrier package may be a Q Growth Carrier Package.

System 1, Part B: Quarantine Growth Workflow, *Mycoplasma* Test
 1. Retrieve from incubator to deck of Quarantine Growth STARlet, remove media from wells to plate for ELISA based *mycoplasma* test.
 2. Manually transfer 96-well assay plates to Quarantine Assay STARlet.

System 1, Part C: Quarantine Growth Workflow, After Passing *Mycoplasma* Testing
 1. Expanded fibroblasts distributed into multiple cryovials, capped, transferred to SAM-80° C.

The system components that may be used to perform these automated steps may be selected from the same components used in the Quarantine Growth Workflow, except a STARlet Auto Load may be used. A Spectramax L Reader may be used as a spectral acquisition device.

System 2: Quarantine Assay Workflow
 1. Test using glow luminescence method, Lonza MycoAlert.
 2. Perform luminescence plate read on spectral acquisition device.

The system components that may be used to perform these automated steps include STARlet Manual Load, a Modular Arm for 4/8/12 ch./MPH, 8 channels with 1000 μl Pipetting Channels and an iSWAP Plate Handler, all available from Hamilton Science Robotics. For luminescence assays the BioTek Synergy HT Reader may be used. The system controller may be a Dell PG with a Windows XP operating system. The carrier package may be a Q Growth Carrier Package.

Systems 3, 4, and 5: Thawing, Infection and Identification
Thawing Module and Infection Module
1. Retrieve cryotubes from SAM-80° C. (61, 190)
2. Thaw on warming block (122)
3. Decap (Hamilton Capper Decapper) (126)
4. Add media to dilute cryoprotectants (122)
5. Spin (128)
6. Resuspend in plating data (122)
7. Plate one sample per well of 6-well (62, 122)
8. Move to incubator (130, 132)
9. Fibroblasts recover for about 3-4 days
10. Confluence check on Cyntellect Celigo Cytometer (124)
11. Fibroblast passaging of all wells on the same day for reprogramming (122)
12. In batches, tryspin passage wells (122)
13. Count cells on Cyntellect Celigo Cytometer (124)
14. Plate a defined number per well on one-to-three wells of a 24-well plate consolidating samples onto as few as 24-well plates as possible (64, 122)
15. Return plates to the incubator overnight (130, 132)
16. Retrieve plates and thaw virus in tube format and add to each well of the fibroblasts in the 24-well plates (130, 122)
17. Daily partial media exchanges (122)
Magnetic Sorting Module
18. Harvest cultures with accutase to single-cell suspension (134)
19. Dilute in staining buffer (134)
20. Stain with magnetic beads against fibroblast surface marker (134)
21. Wash step (134)
22. Apply to magnet (for Dynal beads) or column (for Miltenyi system) (134, 136)
23. Retrieve non-magnetic fraction to new wells (134)
24. Count cells on Cyntellect Celigo Cytometer (124)
25. Dilute to appropriate cell density for delivering 1-10 cells per well to 96-well plate in passaging media (66, 134)
26. Retrieve new Matrigel or matrix-coated 96-well plate from 4° C. incubator (142)
27. Distribute cells to 96-well matrix plates, number based on cell count for example, two per plates per infection (66, 134)
28. Return plates to incubator (132)
29. Daily partial media exchanges (122)
Colony Identification Module
30. Retrieve 96-well plates from incubator to Colony identification liquid handler (66, 132, 138)
31. Perform live cell stain with pluripotency surface marker (138)
32. Image on Cyntellect Celigo Cytometer (140)
33. Identify wells with a single-marker positive colony that has a sharp colony border (140).
34. Techs review hits and select 6 per original sample for passage and retrieve plate and positive well IDs.
35. Cherry-pick wells with single positive colonies (138)
36. Retrieve new Matrigel or matrix coated 96-well plate from 4° C. incubator (68, 142)
37. Harvest selected wells and passage to new 96-well matrix plate consolidating clones onto as few plates as possible and plating each in passaging media (68, 138)
38. Daily partial media exchanges (122)

The system components that may be used to perform these automated steps may be selected from the same components used in the Quarantine Growth Workflow with the addition of one or more CORE 96 PROBEHEAD II 1000 µl model probe heads.

Systems 6, 7, and 8: Maintenance, QC, Expansion, and Freezing
Maintenance Module
39. Will serially-passage clones 1:1 into new 96-well matrix-coated plates until colony density is high enough (68-72, 160)
40. Daily feeding of all plates with ~75% media exchange with 96-tip head (160)
41. Periodic monitoring of colony density and growth rates on Cyntellect Celigo Cytometer (166)
42. Plate replication to produce plates for QC of clones (74-86, 160)
43. Goal is to expand clones onto multiple plates for use in several QC assays to eliminate poorly-performing clones until left with two-to-three high-quality clones per original sample
44. Will also cherry-pick and re-array clones that pass QC steps as the poor clones are eliminated to consolidate clones onto as few plates as possible (80, 86, 160)
45. Daily feeding throughout this process (160)
QC Module
46. Harvest cells (74, 150)
47. Count cells (164)
48. Plate a defined cell number in V-bottom plates (range of 5000-10000 cells/well) in 2-6 replicates per line (84, 150)
49. Return to incubator—(1 g aggregation) (172)
50. Media exchange after two days (150)
51. Incubate for additional 12 days in incubator (172)
52. Partial media exchange every two days (150)
53. Transfer to nucleic acid prep station to remove media from wells leaving embryoid bodies in the well (84, 192)
54. Resuspend in RNA lysis buffer and combine and mix replicates for each sample and make plates available for analysis in Nanostring nCounter assay (84, 192)
Freezing Module
55. Begins with a 96-well plate after an expansion passage (88)
56. Incubate 6 days in incubator (172)
57. Partial media exchange every day (154)
58. Remove plate from incubator (88, 162)
59. Remove media (needs to be complete) (154)
60. Add cool Pre-freeze media (diluted matrigel in growth media) (154)
61. Incubate in incubator for 1 h (172)
62. Remove media (needs to be complete) (154)
63. Addition of cold freezing media—low volume (154)
64. Seal plate (88, 164)
65. Samples taken off-line to −80° C. storage to freeze (190)
66. Store in vapor phase Liquid Nitrogen
Cryovial Storage
67. Begins with a 96-well plate after an expansion passage (90)
68. Incubate 6 days (172)
69. Daily partial media exchanges (154)
70. Passage wells 1:1 to a 24-well plate (92, 154)
71. Incubate 6 days (172)
72. Daily partial media exchanges (154)
73. Passage wells 1:1 to a 6-well plate (94, 154)
74. Incubate 4-6 days (172)
75. Daily partial media exchanges (154)
76. Remove plate from incubator (162)

77. Partial media exchange with pre-freeze media (154)
78. Incubate in incubator for 1 h (172)
79. Harvest cells for freezing as for normal passage (154)
80. Move to matrix tubes, two-to-three tubes per well (96, 154)
81. Spin and remove media (168, 154)
82. Addition of cold freezing media (154)
83. Cap tubes (170)
84. Samples taken off-line to −80° C. storage (190)

The system components that may be used to perform these automated steps may be selected from the same components used in the Quarantine Growth Workflow.

As used herein "adult" means post-fetal, i.e., an organism from the neonate stage through the end of life, and includes, for example, cells obtained from delivered placenta tissue, amniotic fluid and/or cord blood.

As used herein, the term "adult differentiated cell" encompasses a wide range of differentiated cell types obtained from an adult organism, that are amenable to producing iPSCs using the instantly described automation system. Preferably, the adult differentiated cell is a "fibroblast." Fibroblasts, also referred to as "fibrocytes" in their less active form, are derived from mesenchyme. Their function includes secreting the precursors of extracellular matrix components including, e.g., collagen. Histologically, fibroblasts are highly branched cells, but fibrocytes are generally smaller and are often described as spindle-shaped. Fibroblasts and fibrocytes derived from any tissue may be employed as a starting material for the automated workflow system on the invention.

As used herein, the term, "induced pluripotent stem cells" or, iPSCs, means that the stem cells are produced from differentiated adult cells that have been induced or changed, i.e., reprogrammed into cells capable of differentiating into tissues of all three germ or dermal layers: mesoderm, endoderm, and ectoderm. The iPSCs produced do not refer to cells as they are found in nature.

Mammalian somatic cells useful in the present invention include, by way of example, adult stem cells, sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other known muscle cells, and generally any live somatic cells. In particular embodiments, fibroblasts are used. The term somatic cell, as used herein, is also intended to include adult stem cells. An adult stem cell is a cell that is capable of giving rise to all cell types of a particular tissue. Exemplary adult stem cells include hematopoietic stem cells, neural stem cells, and mesenchymal stem cells.

One advantage of the present invention is that it provides an essentially limitless supply of isogenic or synegenic human cells suitable for transplantation, use in drug discovery assays, or for disease modeling. The iPSCs are tailored specifically to the patient, avoiding immune rejection. Therefore, it will obviate the significant problem associated with current transplantation methods, such as, rejection of the transplanted tissue, which may occur because of host versus graft or graft versus host rejection. When utilized for drug discovery the cells demonstrate each person's response to chemicals when used in drug discovery or their individual manifestation of diseases in disease models. Several kinds of iPSCs or fully differentiated somatic cells prepared from iPSCs derived from somatic cells derived from humans can be stored in an iPSC bank as a library of cells, and one kind or more kinds of the iPSCs in the library can be used for preparation of somatic cells, tissues, or organs that are free of rejection by a patient to be subjected to stem cell therapy.

The iPSCs of the present invention may be differentiated into a number of different cell types to treat a variety of disorders by methods known in the art. For example, iPSCs may be induced to differentiate into hematopoetic stem cells, muscle cells, cardiac muscle cells, liver cells, cartilage cells, epithelial cells, urinary tract cells, neuronal cells, and the like. The differentiated cells may then be transplanted back into the patient's body to prevent or treat a condition or used to advance medical research or in to develop drug discovery assays. Thus, the methods of the present invention may be used to as a treatment or to develop a treatment for a subject having a myocardial infarction, congestive heart failure, stroke, ischemia, peripheral vascular disease, alcoholic liver disease, cirrhosis, Parkinson's disease, Alzheimer's disease, diabetes, cancer, arthritis, wound healing, immunodeficiency, aplastic anemia, anemia, Huntington's disease, amyotrophic lateral sclerosis (ALS), lysosomal storage diseases, multiple sclerosis, spinal cord injuries, genetic disorders, and similar diseases, where an increase or replacement of a particular cell type/tissue or cellular de-differentiation is desirable.

The term "totipotency" refers to a cell with a developmental potential to make all of the cells in the adult body as well as the extra-embryonic tissues, including the placenta. The fertilized egg (zygote) is totipotent, as are the cells (blastomeres) of the morula (up to the 16-cell stage following fertilization).

The term "pluripotent" as used herein refers to a cell with the developmental potential, under different conditions, to differentiate to cell types characteristic of all three germ cell layers, i.e., endoderm (e.g., gut tissue), mesoderm (including blood, muscle, and vessels), and ectoderm (such as skin and nerve). A pluripotent cell has a lower developmental potential than a totipotent cell. The ability of a cell to differentiate to all three germ layers can be determined using, for example, a nude mouse teratoma formation assay. In some embodiments, pluripotency can also evidenced by the expression of embryonic stem (ES) cell markers, although the preferred test for pluripotency of a cell or population of cells generated using the compositions and methods described herein is the demonstration that a cell has the developmental potential to differentiate into cells of each of the three germ layers. In some embodiments, a pluripotent cell is termed an "undifferentiated cell." Accordingly, the terms "pluripotency" or a "pluripotent state" as used herein refer to the developmental potential of a cell that provides the ability for the cell to differentiate into all three embryonic germ layers (endoderm, mesoderm and ectoderm). Those of skill in the art are aware of the embryonic germ layer or lineage that gives rise to a given cell type. A cell in a pluripotent state typically has the potential to divide in vitro for a long period of time, e.g., greater than one year or more than 30 passages.

The term "multipotent" when used in reference to a "multipotent cell" refers to a cell that has the developmental potential to differentiate into cells of one or more germ layers, but not all three. Thus, a multipotent cell can also be termed a "partially differentiated cell." Multipotent cells are well known in the art, and examples of multipotent cells include adult stem cells, such as for example, hematopoietic stem cells and neural stem cells. "Multipotent" indicates that a cell may form many types of cells in a given lineage, but not cells of other lineages. For example, a multipotent hematopoietic cell can form the many different types of blood cells (red, white, platelets, etc.), but it cannot form neurons. Accordingly, the term "multipotency" refers to a state of a cell with a degree of developmental potential that is less than totipotent and pluripotent.

The terms "stem cell" or "undifferentiated cell" as used herein, refer to a cell in an undifferentiated or partially differentiated state that has the property of self-renewal and has the developmental potential to differentiate into multiple cell types, without a specific implied meaning regarding developmental potential (i.e., totipotent, pluripotent, multipotent, etc.). A stem cell is capable of proliferation and giving rise to more such stem cells while maintaining its developmental potential. In theory, self-renewal can occur by either of two major mechanisms. Stem cells can divide asymmetrically, which is known as obligatory asymmetrical differentiation, with one daughter cell retaining the developmental potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. While each of these multipotent cells may be considered stem cells, the range of cell types each such stem cell can give rise to, i.e., their developmental potential, can vary considerably. Alternatively, some of the stem cells in a population can divide symmetrically into two stem cells, known as stochastic differentiation, thus maintaining some stem cells in the population as a whole, while other cells in the population give rise to differentiated progeny only. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. In some embodiments, the term stem cell refers generally to a naturally occurring parent cell whose descendants (progeny cells) specialize, often in different directions, by differentiation, e.g., by acquiring completely individual characters, as occurs in progressive diversification of embryonic cells and tissues. Some differentiated cells also have the capacity to give rise to cells of greater developmental potential. Such capacity may be natural or may be induced artificially upon treatment with various factors. Cells that begin as stem cells might proceed toward a differentiated phenotype, but then can be induced to "reverse" and re-express the stem cell phenotype, a term often referred to as "dedifferentiation" or "reprogramming" or "retrodifferentiation" by persons of ordinary skill in the art.

The term "embryonic stem cell" as used herein refers to naturally occurring pluripotent stem cells of the inner cell mass of the embryonic blastocyst (see, for e.g., U.S. Pat. Nos. 5,843,780; 6,200,806; 7,029,913; 7,584,479, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). Embryonic stem cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta, i.e., are not totipotent.

As used herein, the distinguishing characteristics of an embryonic stem cell define an "embryonic stem cell phenotype." Accordingly, a cell has the phenotype of an embryonic stem cell if it possesses one or more of the unique characteristics of an embryonic stem cell, such that that cell can be distinguished from other cells not having the embryonic stem cell phenotype. Exemplary distinguishing embryonic stem cell phenotype characteristics include, without limitation, expression of specific cell-surface or intracellular markers, including protein and microRNAs, gene expression profiles, methylation profiles, deacetylation profiles, proliferative capacity, differentiation capacity, karyotype, responsiveness to particular culture conditions, and the like. In some embodiments, the determination of whether a cell has an "embryonic stem cell phenotype" is made by comparing one or more characteristics of the cell to one or more characteristics of an embryonic stem cell line cultured within the same laboratory.

The term "somatic stem cell" is used herein to refer to any pluripotent or multipotent stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Each of these somatic stem cells can be characterized based on gene expression, factor responsiveness, and morphology in culture. Exemplary naturally occurring somatic stem cells include, but are not limited to, neural stem cells, neural crest stem cells, mesenchymal stem cells, hematopoietic stem cells, and pancreatic stem cells. In some aspects described herein, a "somatic pluripotent cell" refers to a somatic cell, or a progeny cell of the somatic cell, that has had its developmental potential altered, i.e., increased, to that of a pluripotent state by contacting with, or the introduction of, one or more reprogramming factors using the compositions and methods described herein.

The term "progenitor cell" is used herein to refer to cells that have greater developmental potential, i.e., a cellular phenotype that is more primitive (e.g., is at an earlier step along a developmental pathway or progression) relative to a cell which it can give rise to by differentiation. Often, progenitor cells have significant or very high proliferative potential.

Progenitor cells can give rise to multiple distinct cells having lower developmental potential, i.e., differentiated cell types, or to a single differentiated cell type, depending on the developmental pathway and on the environment in which the cells develop and differentiate.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cell forming the body of an organism, as opposed to a germline cell. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated, pluripotent, embryonic stem cells—is a somatic cell: internal organs, skin, bones, blood, and connective tissue are all made up of somatic cells. In some embodiments the somatic cell is a "non-embryonic somatic cell," by which is meant a somatic cell that is not present in or obtained from an embryo and does not result from proliferation of such a cell in vitro. In some embodiments the somatic cell is an "adult somatic cell," by which is meant a cell that is present in or obtained from an organism other than an embryo or a fetus or results from proliferation of such a cell in vitro. Unless otherwise indicated, the compositions and methods for reprogramming a somatic cell described herein can be performed both in vivo and in vitro (where in vivo is practiced when a somatic cell is present within a subject, and where in vitro is practiced using an isolated somatic cell maintained in culture).

The term "differentiated cell" encompasses any somatic cell that is not, in its native form, pluripotent, as that term is defined herein. Thus, the term a "differentiated cell" also encompasses cells that are partially differentiated, such as multipotent cells, or cells that are stable, non-pluripotent partially reprogrammed, or partially differentiated cells, generated using any of the compositions and methods described herein. In some embodiments, a differentiated cell is a cell that is a stable intermediate cell, such as a non-pluripotent, partially reprogrammed cell. It should be noted that placing many primary cells in culture can lead to some loss of fully differentiated characteristics. Thus, simply culturing such differentiated or somatic cells does not render these cells non-differentiated cells (e.g., undifferentiated cells) or pluripotent cells. The transition of a differentiated cell (including stable, non-pluripotent partially reprogrammed cell intermediates) to pluripotency requires a reprogramming stimulus beyond the stimuli that lead to partial loss of differentiated character upon placement in culture. Reprogrammed and, in some embodiments, partially reprogrammed cells, also have the characteristic of having the capacity to undergo extended passaging without loss of growth potential, relative to parental cells having lower developmental potential, which generally have capacity for only a limited number of divisions in culture. In some embodiments, the term "differentiated cell" also refers to a cell of a more specialized cell type (i.e., decreased developmental potential) derived from a cell of a less specialized cell type (i.e., increased developmental potential) (e.g., from an undifferentiated cell or a reprogrammed cell) where the cell has undergone a cellular differentiation process.

The term "reprogramming" as used herein refers to a process that reverses the developmental potential of a cell or population of cells (e.g., a somatic cell). Stated another way, reprogramming refers to a process of driving a cell to a state with higher developmental potential, i.e., backwards to a less differentiated state. The cell to be reprogrammed can be either partially or terminally differentiated prior to reprogramming. In some embodiments of the aspects described herein, reprogramming encompasses a complete or partial reversion of the differentiation state, i.e., an increase in the developmental potential of a cell, to that of a cell having a pluripotent state. In some embodiments, reprogramming encompasses driving a somatic cell to a pluripotent state, such that the cell has the developmental potential of an embryonic stem cell, i.e., an embryonic stem cell phenotype. In some embodiments, reprogramming also encompasses a partial reversion of the differentiation state or a partial increase of the developmental potential of a cell, such as a somatic cell or a unipotent cell, to a multipotent state. Reprogramming also encompasses partial reversion of the differentiation state of a cell to a state that renders the cell more susceptible to complete reprogramming to a pluripotent state when subjected to additional manipulations, such as those described herein. Such manipulations can result in endogenous expression of particular genes by the cells, or by the progeny of the cells, the expression of which contributes to or maintains the reprogramming. In certain embodiments, reprogramming of a cell using the synthetic, modified RNAs and methods thereof described herein causes the cell to assume a multipotent state (e.g., is a multipotent cell). In some embodiments, reprogramming of a cell (e.g., a somatic cell) using the synthetic, modified RNAs and methods thereof described herein causes the cell to assume a pluripotent-like state or an embryonic stem cell phenotype. The resulting cells are referred to herein as "reprogrammed cells," "somatic pluripotent cells," and "RNA-induced somatic pluripotent cells." The term "partially reprogrammed somatic cell" as referred to herein refers to a cell which has been reprogrammed from a cell with lower developmental potential by the methods as disclosed herein, such that the partially reprogrammed cell has not been completely reprogrammed to a pluripotent state but rather to a non-pluripotent, stable intermediate state. Such a partially reprogrammed cell can have a developmental potential lower that a pluripotent cell, but higher than a multipotent cell, as those terms are defined herein. A partially reprogrammed cell can, for example, differentiate into one or two of the three germ layers, but cannot differentiate into all three of the germ layers.

The term a "reprogramming factor," as used herein, refers to a developmental potential altering factor, as that term is defined herein, such as a gene, protein, RNA, DNA, or small molecule, the expression of which contributes to the reprogramming of a cell, e.g., a somatic cell, to a less differentiated or undifferentiated state, e.g., to a cell of a pluripotent state or partially pluripotent state. A reprogramming factor can be, for example, transcription factors that can reprogram cells to a pluripotent state, such as SOX2, OCT3/4, KLF4, NANOG, LIN-28, c-MYC, and the like, including as any gene, protein, RNA or small molecule, that can substitute for one or more of these in a method of reprogramming cells in vitro. In some embodiments, exogenous expression of a reprogramming factor, using the synthetic modified RNAs and methods thereof described herein, induces endogenous expression of one or more reprogramming factors, such that exogenous expression of one or more reprogramming factors is no longer required for stable maintenance of the cell in the reprogrammed or partially reprogrammed state. "Reprogramming to a pluripotent state in vitro" is used herein to refer to in vitro reprogramming methods that do not require and/or do not include nuclear or cytoplasmic transfer or cell fusion, e.g., with oocytes, embryos, germ cells, or pluripotent cells. A reprogramming factor can also be termed a "de-differentiation factor," which refers to a developmental potential altering factor, as that term is defined herein, such as a protein or RNA, that induces a cell to de-differentiate to a less differentiated phenotype, that is a de-differentiation factor increases the developmental potential of a cell.

As used herein, the term "differentiation factor" refers to a developmental potential altering factor, as that term is defined herein, such as a protein, RNA, or small molecule, that induces a cell to differentiate to a desired cell-type, i.e., a differentiation factor reduces the developmental potential of a cell. In some embodiments, a differentiation factor can be a cell-type specific polypeptide, however this is not required. Differentiation to a specific cell type can require simultaneous and/or successive expression of more than one differentiation factor. In some aspects described herein, the developmental potential of a cell or population of cells is first increased via reprogramming or partial reprogramming using synthetic, modified RNAs, as described herein, and then the cell or progeny cells thereof produced by such reprogramming are induced to undergo differentiation by contacting with, or introducing, one or more synthetic, modified RNAs encoding differentiation factors, such that the cell or progeny cells thereof have decreased developmental potential.

In the context of cell ontogeny, the term "differentiate", or "differentiating" is a relative term that refers to a developmental process by which a cell has progressed further down a developmental pathway than its immediate precursor cell. Thus in some embodiments, a reprogrammed cell as the term is defined herein, can differentiate to a lineage-restricted precursor cell (such as a mesodermal stem cell), which in turn can differentiate into other types of precursor cells further down the pathway (such as a tissue specific precursor, for example, a cardiomyocyte precursor), and then to an end-stage differentiated cell, which plays a characteristic role in a certain tissue type, and may or may not retain the capacity to proliferate further.

As used herein, the term "without the formation of a pluripotent intermediate cell" refers to the transdifferentiation of one cell type to another cell type, preferably, in one step; thus a method that modifies the differentiated phenotype or developmental potential of a cell without the formation of a pluripotent intermediate cell does not require that the cell be first dedifferentiated (or reprogrammed) and then differentiated to another cell type. Instead, the cell type is merely "switched" from one cell type to another without going through a less differentiated phenotype. Accordingly, transdifferentiation refers to a change in the developmental potential of a cell whereby the cell is induced to become a different cell having a similar developmental potential, e.g., a liver cell to a pancreatic cell, a pancreatic alpha cell into a pancreatic beta cell, etc. The system and methods of the invention are well suited for transdifferentiation of cells.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene, and polypeptides obtained by translation of mRNA transcribed from a gene. In some embodiments, an expression product is transcribed from a sequence that does not encode a polypeptide, such as a microRNA.

As used herein, the term "transcription factor" refers to a protein that binds to specific parts of DNA using DNA binding domains and is part of the system that controls the transcription of genetic information from DNA to RNA.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "exogenous" as used herein refers to a nucleic acid (e.g., a synthetic, modified RNA encoding a transcription factor), or a protein (e.g., a transcription factor) that has been introduced by a process involving the hand of man into a biological system such as a cell or organism in which it is not normally found, or in which it is found in lower amounts. A factor (e.g., a synthetic, modified RNA encoding a transcription factor, or a protein, e.g., a polypeptide) is considered exogenous if it is introduced into an immediate precursor cell or a progeny cell that inherits the substance. In contrast, the term "endogenous" refers to a factor or expression product that is native to the biological system or cell (e.g., endogenous expression of a gene, such as, e.g., SOX2 refers to production of a SOX2 polypeptide by the endogenous gene in a cell). In some embodiments, the introduction of one or more exogenous factors to a cell, e.g., a developmental potential altering factor, using the compositions and methods comprising synthetic, modified RNAs described herein, induces endogenous expression in the cell or progeny cell(s) thereof of a factor or gene product necessary for maintenance of the cell or progeny cell(s) thereof in a new developmental potential.

The term "isolated cell" as used herein refers to a cell that has been removed from an organism in which it was originally found, or a descendant of such a cell. Optionally the cell has been cultured in vitro, e.g., in the presence of other cells. Optionally, the cell is later introduced into a second organism or re-introduced into the organism from which it (or the cell or population of cells from which it descended) was isolated.

The term "isolated population" with respect to an isolated population of cells as used herein refers to a population of cells that has been removed and separated from a mixed or heterogeneous population of cells. In some embodiments, an isolated population is a "substantially pure" population of cells as compared to the heterogeneous population from which the cells were isolated or enriched. In some embodiments, the isolated population is an isolated population of pluripotent cells which comprise a substantially pure population of pluripotent cells as compared to a heterogeneous population of somatic cells from which the pluripotent cells were derived.

As used herein, the terms "synthetic, modified RNA" or "modified RNA" refer to an RNA molecule produced in vitro, which comprise at least one modified nucleoside as that term is defined herein below. Methods of the invention do not require modified RNA. The synthetic, modified RNA composition does not encompass mRNAs that are isolated from natural sources such as cells, tissue, organs etc., having those modifications, but rather only synthetic, modified RNAs that are synthesized using in vitro techniques. The term "composition," as applied to the terms "synthetic, modified RNA" or "modified RNA," encompasses a plurality of different synthetic, modified RNA molecules (e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40, at least 50, at least 75, at least 90, at least 100 synthetic, modified RNA molecules or more). In some embodiments, a synthetic, modified RNA composition can further comprise other agents (e.g., an inhibitor of interferon expression or activity, a transfection reagent, etc.). Such a plurality can include synthetic, modified RNA of different sequences (e.g., coding for different polypeptides), synthetic, modified RNAs of the same sequence with differing modifications, or any combination thereof.

As used herein, the term "polypeptide" refers to a polymer of amino acids comprising at least 2 amino acids (e.g., at least 5, at least 10, at least 20, at least 30, at least 40, at least 50, at least 60, at least 70, at least 80, at least 90, at least 100, at least 125, at least 150, at least 175, at least 200, at least 225, at least 250, at least 275, at least 300, at least 350, at least 400, at least 450, at least 500, at least 600, at least 700, at least 800, at least 900, at least 1000, at least 2000, at least 3000, at least 4000, at least 5000, at least 6000, at least 7000, at least 8000, at least 9000, at least 10,000 amino acids or more). The terms "protein" and "polypeptide" are used interchangeably herein. As used herein, the term "peptide" refers to a relatively short polypeptide, typically between about 2 and 60 amino acids in length.

In one embodiment, the inventive system can also be used to obtain cell populations enriched in fully reprogrammed cells, from among cells that have undergone differentiation in established iPSC cell lines that were cultured under both murine embryonic fibroblast (MEF) feeder layer, as well as feeder reconditions. The inventive system further enables the live-sorting of defined subpopulations of fully-reprogrammed, or differentiated, iPSC cells into 96-well plates for use in high-throughput screening campaigns.

FIG. 1 shows the steps performed by System 1, including plating of a biopsy (2), outgrowth and passaging (4) (rolling production on liquid handling robot), QC (6) (automated testing for mycoplasma), and (8) automated freezing on liquid handling robot.

Figure 2:
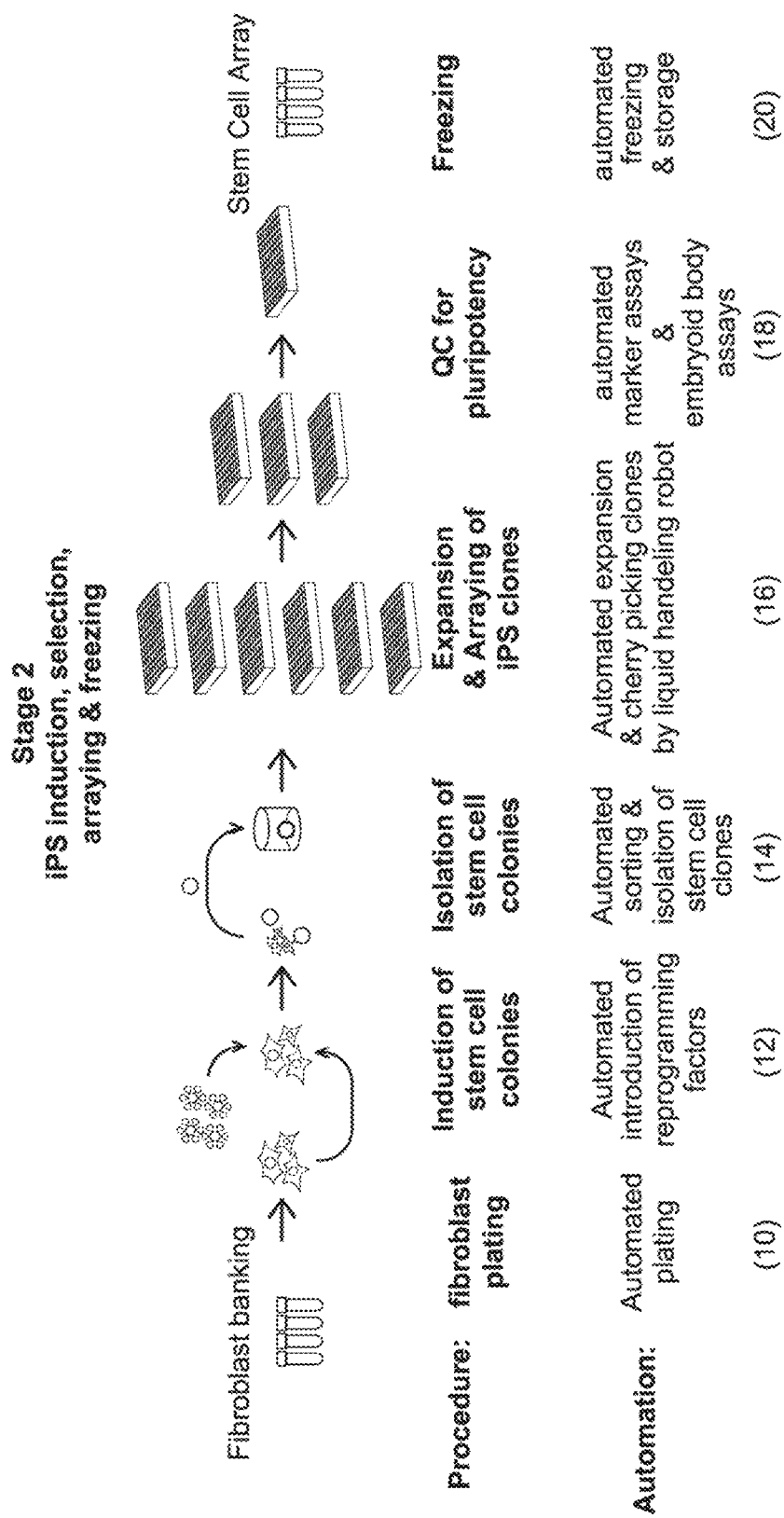
FIG. 2 shows steps for obtaining a stem cell array from a fibroblast bank.

FIG. 2 shows the steps performed by Systems 2, 3, and 4. Fibroblasts are plated by the automated system (10), reprogramming factors are introduced by the automated system (12), iPSCs are isolated by automated sorting and isolation (14), desired clones are selected and expanded by the automated system (16), automated quality checks (QC) for pluripotent status by marker assays and embryoid body assays (18), followed by automated freezing and storage of desired cells (20).

Figure 3:
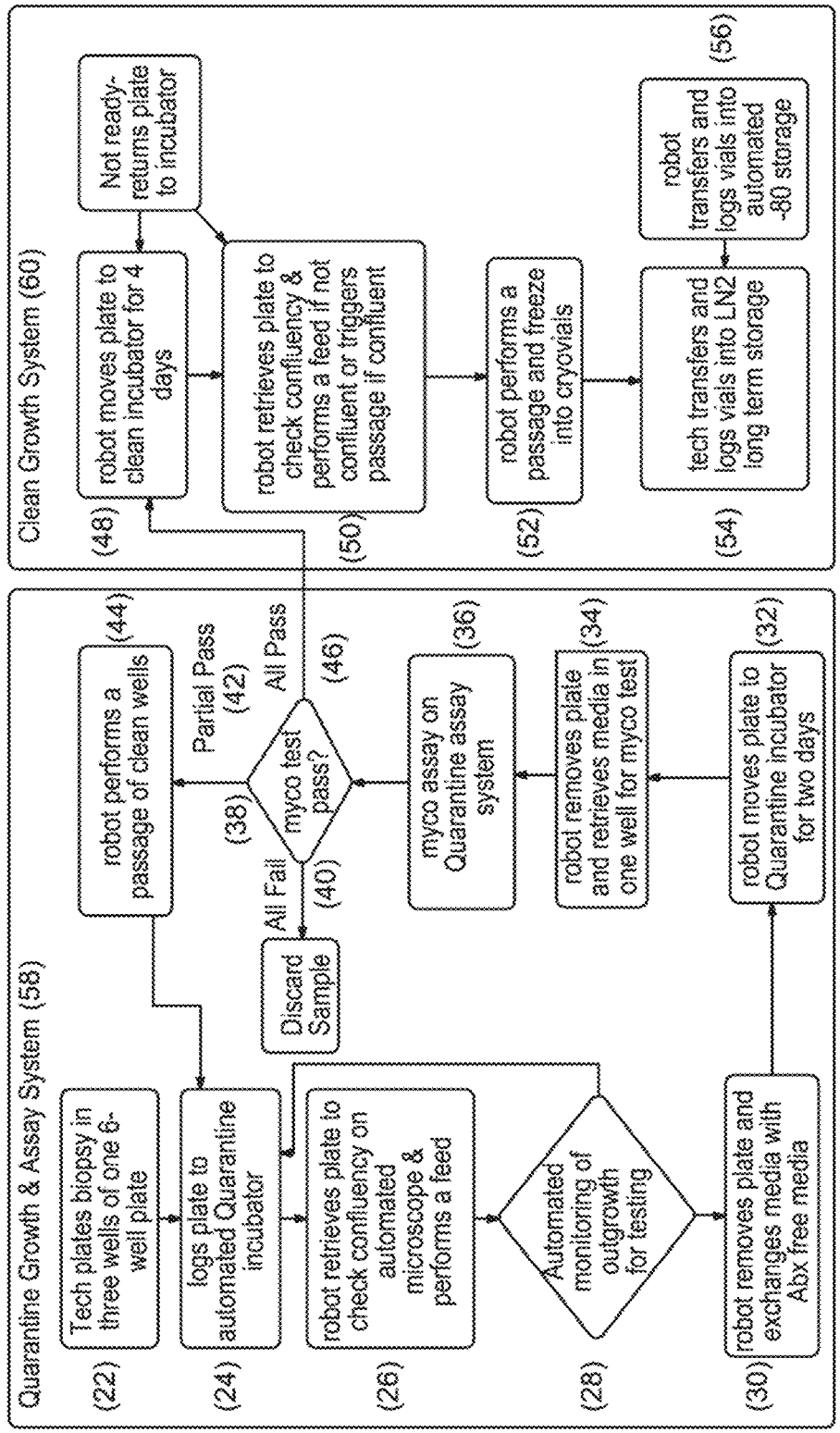
FIG. 3 is a flowchart showing steps in a system for producing iPSCs.

FIG. 3 is a flowchart showing the step (22) through (60) involved in System 1.

FIG. 3 illustrates an example of the workflow and decision tree for production of fibroblasts from biopsies. The workflow is divided into Quarantine (58) and Clean phases (60). As biopsies enter the facility, a technician plates biopsies in 6-well plates (22) and logs the plates into the automated incubator (24). After biopsies are given time to attach to the plate, the liquid handling robot retrieves the plates from the automated incubator to feed and check confluence of the outgrowths on an automated microscope (26). The plates are returned to the incubator and allowed to outgrow (28). The liquid handler removes the plate from the incubator and exchanges the media for antibiotic and antimycotic free media (30). The robot moves the plate to the incubator for another five days (32). The robot then removes the plate and retrieves media to daughter plates for mycoplasma test (34). The daughter plates are moved to the Quarantine Assay system for mycoplasma testing (36). A choice is then made based on a positive signal from the assay (38). If all wells of a 6-well plate fail with a positive mycoplasma assay result (40) they are discarded. If all wells of a 6-well plate are negative and free of mycoplasma, they are transferred out of quarantine into the clean growth system (46). If some wells are positive and some wells are negative, the negative wells are maintained in quarantine (42). The negative wells are passaged (44) to new plates, transferred to the incubator, and the source plates containing positive wells are discarded. These cultures proceed through steps to retest for mycoplasma (24, 26, 28, 30, 32, 34, 36, 38). Clean cultures are monitored for growth (50), passaged (52) and frozen in cryovials (54, 56).

Figure 4A:
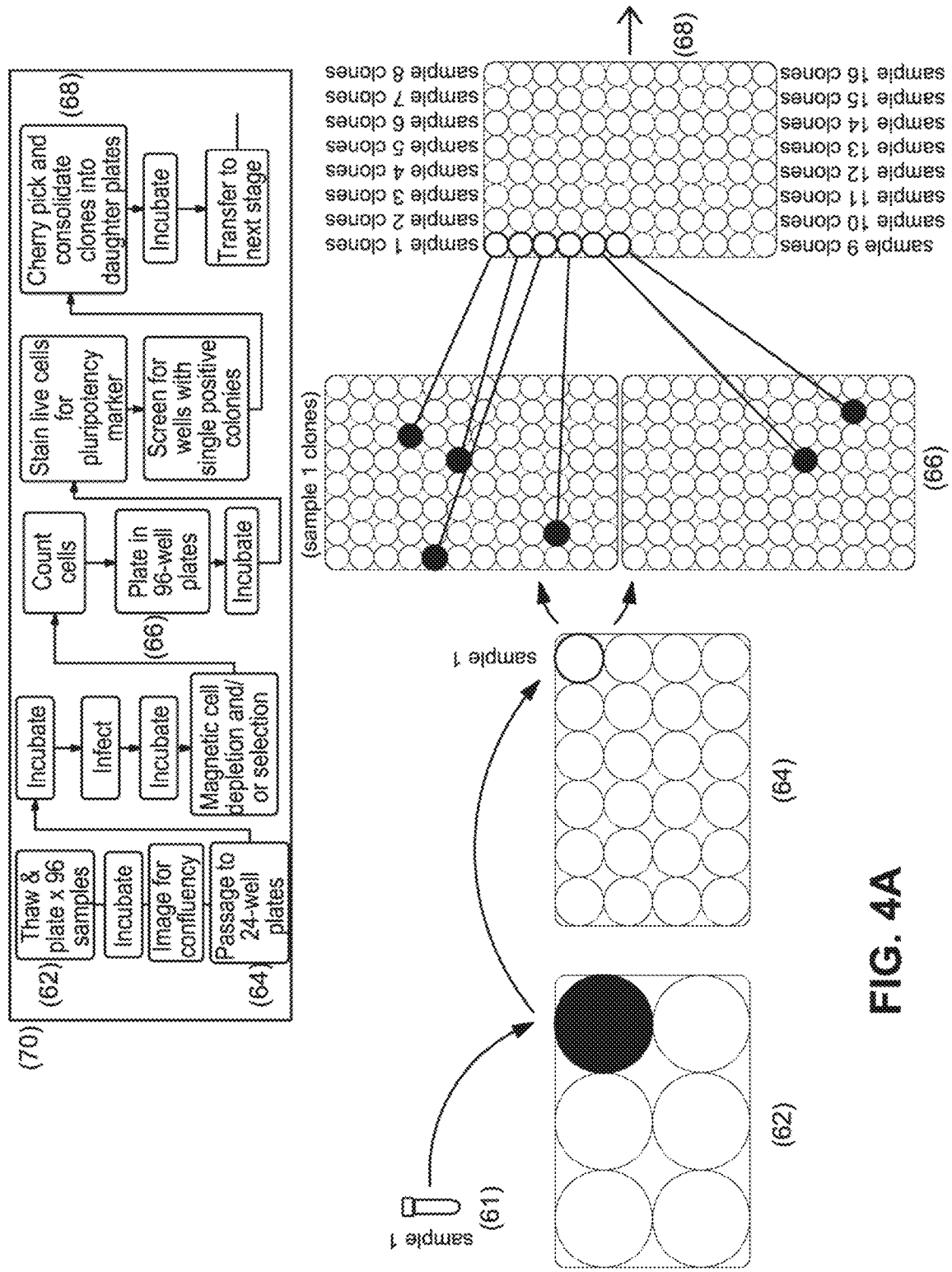

FIGS. 4A, 4B1, 4B2, and 4C illustrate an example of the flow of patient samples through multi-well tissue culture plates during the automated reprogramming process. At the top of each diagram, a flowchart describes the flow of procedures performed at each step of the workflow (70, 88, 98). At the bottom of each diagram, multi-well cell culture plates are shown with platemaps for example samples represented by shaded wells or groups of wells marked with sample labels (61-68, 72-86, 88-96). Transfer of a sample from plate-to-plate or well-to-well through the procedure is shown from left to right as indicated by arrows. As shown in FIG. 4A, the automated iPSC derivation process begins when patient samples and control fibroblast samples (61) are plated in individual wells of a 6-well plate (62). These are passaged at defined cell number into individual wells of a 24-well plate (64) for infection using viruses encoding reprogramming factors or other means of introducing reprogramming factors to the cells. In the next step, reprogrammed samples are depleted of non-reprogrammed cells by cell sorting or, as is preferred, using magnetic bead based enrichment and plated at clonal density in multiple wells in 96-well plates (66). Two such plates are shown in this example. In this example, 6 wells, as indicated by wells with a dot in the middle (66) are identified containing a single clone positive for a pluripotency surface marker as assayed by immunofluorescent analysis on automated imager. These clones are passaged and cherry picked to reformat the clones into a minimum number of 96-well plates (68). The example figure shows six clones per individual starting sample and indicates that clones from 16 starting sample can be arrayed onto a 96-well plate. To facilitate plate processing, this cherry picking step can be performed over multiple passages to consolidate the clones onto a minimum number of plates. As show in FIGS. 4B1 and 4B2, these clones are serially passaged until confluence of stem cell colonies within a well is achieved for each starting sample (72). Each plates' samples are then replicated onto duplicate plates (74-86), to allow for the quality control (6) and selection of clones that demonstrate appropriate stem cell characteristics. To begin the QC process, one plate is generated by the system for a Pluripotency quality control assay needed to determine pluripotent status of the individual clones (74) and one plate is generated for carrying forward in subsequent passages (76). The plate that is carried forward is passaged again into three plates (78, 80, 82) for further quality control and expansion. One plate is harvested for QC assays to characterize Karyotype and genetic diversity (78). A second plate (82) is passaged onto v-bottom plates to form embryoid bodies (84) for a QC assay that assesses differentiation capability of the iPS clones. The final plate (80) is carried forward for further expansion. Individual clones that do not pass quality control from previous pluripotency QC assays are not carried forward as shown by the "X" in the wells indicated in FIG. 4. In the example shown in FIG. 4B2, the consolidated plate (86) will contain iPS lines (or differentiated lines) from up to 32 individuals represented by 3 iPS clones per individual on a single 96 well plate or up to 96 individuals if represented by a single clone each. Remaining clones are consolidated onto as few plates as possible until one to three clones remain (86-92).

Figure 4C:
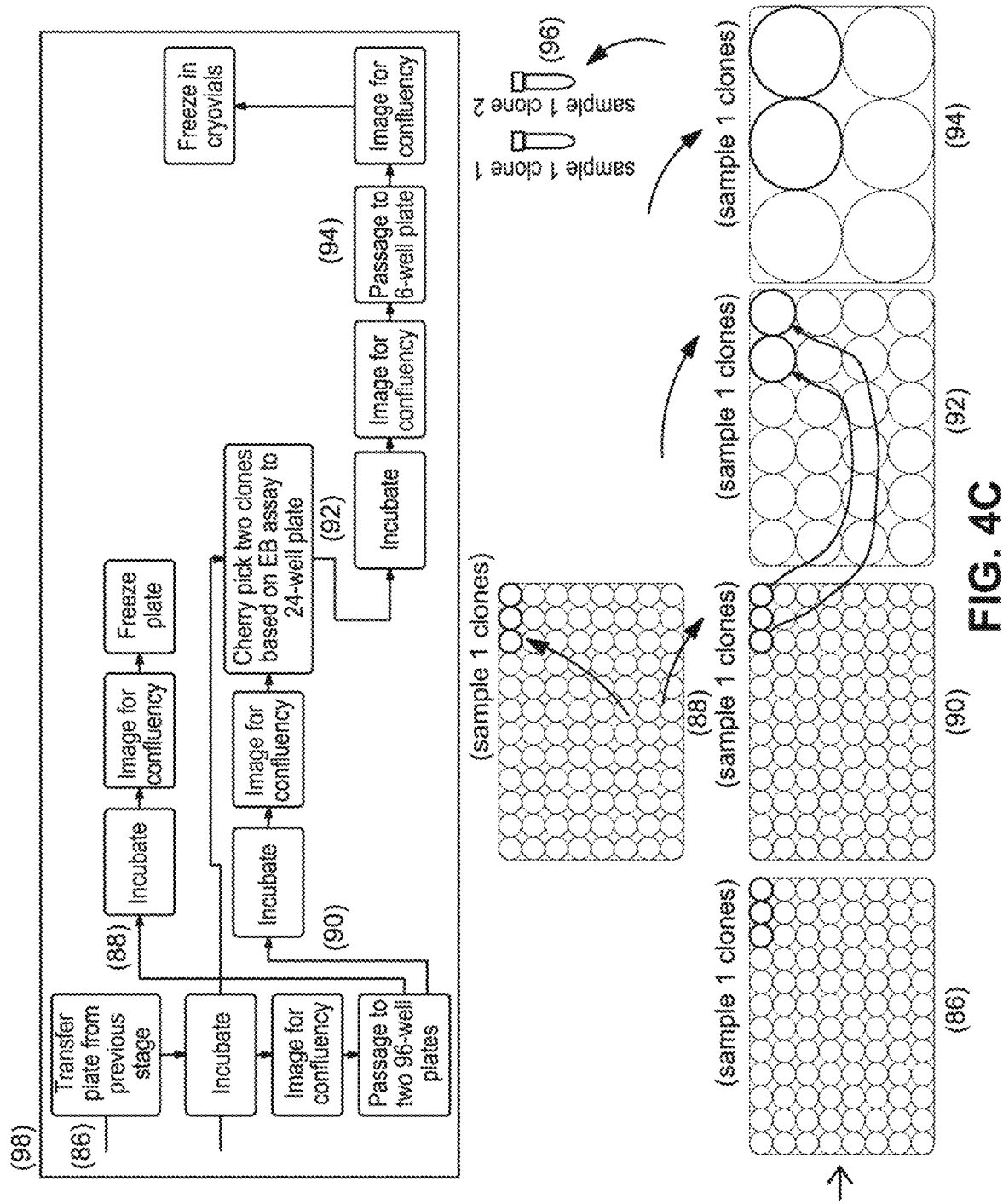

As shown in FIG. 4C, these are expanded for cryopreservation while attached to the plate (88) or further expanded (92-94) and cryopreserved in cryovials (96).

Methods for transfecting and transforming or reprogramming adult cells to form iPSC lines are generally known, e.g., Takahashi et al., 2007 *Cell*, 131: 861-872, 2007, Yu et al., 2007, *Science*, vol. 318, pp. 1917-1920. iPSC are induced from somatic cells by somatic cells of interest with reprogramming factors. Reprogramming factors are contemplated to include, e.g., transcription factors. The method for reprogramming adult cells includes, e.g., introducing and expressing a combination of specific transcription factors, e.g., a combination of Oct3/4, Sox2, Klf4 and c-Myc genes. Others have demonstrated that other transcription factors may be employed in transforming or reprogramming adult cells. These other transcription factors include, e.g., Lin28, Nanog, hTert and SV40 large T antigen as described, for example, by Takahashi et al., 2006 *Cell*, 126: 663-676 and Huiqun Yin, et al. 2009, *Front. Agric. China* 3(2): 199-208, incorporated by reference herein.

In another aspect, iPSCs can be generated using direct introduction of RNAs into a cell, which, when translated, provide a desired protein or proteins. Higher eukaryotic cells have evolved cellular defenses against foreign, "non-self," RNA that ultimately result in the global inhibition of cellular protein synthesis, resulting in cellular toxicity. This response involves, in part, the production of Type I or Type II interferons, and is generally referred to as the "interferon response" or the "cellular innate immune response." The cellular defenses normally recognize synthetic RNAs as foreign, and induce this cellular innate immune response. In certain aspects where the ability to achieve sustained or repeated expression of an exogenously directed protein using RNA is hampered by the induction of this innate immune response, it is desirable to use synthetic RNAs that are modified in a manner that avoids or reduces the response. Avoidance or reduction of the innate immune response permit sustained expression from exogenously introduced RNA necessary, for example, to modify the developmental phenotype of a cell. In one aspect, sustained expression is achieved by repeated introduction of synthetic, modified RNAs into a target cell or its progeny. The inventive methods include natural or synthetic RNAs.

The natural, modified, or synthetic RNAs in one aspect, can be introduced to a cell in order to induce exogenous expression of a protein of interest in a cell. The ability to direct exogenous expression of a protein of interest using the modified, synthetic RNAs described herein is useful, for example, in the treatment of disorders caused by an endogenous genetic defect in a cell or organism that impairs or prevents the ability of that cell or organism to produce the protein of interest. Accordingly, in some embodiments, compositions and methods comprising the RNAs described herein can be used for the purposes of gene therapy.

The RNAs described can advantageously be used in the alteration of cellular fates and/or developmental potential. The ability to express a protein from an exogenous RNA permits either the alteration or reversal of the developmental potential of a cell, i.e., the reprogramming of the cell, and the directed differentiation of a cell to a more differentiated phenotype. A critical aspect in altering the developmental potential of a cell is the requirement for sustained and prolonged expression of one or more developmental potential altering factors in the cell or its immediate progeny. Traditionally, such sustained expression has been achieved by introducing DNA or viral vectors to a cell. These approaches have limited therapeutic utility due to the potential for insertional mutagenesis.

One of the areas that can most benefit from the ability to express a desired protein or proteins over a sustained period of time from exogenous RNAs as described herein is the generation of pluripotent or multipotent cells from cells initially having a more differentiated phenotype. In this aspect, RNAs encoding a reprogramming factor or factors are used to reprogram cells to a less differentiated phenotype, i.e., having a greater developmental potential.

A major goal of stem cell technology is to make the stem cell differentiate into a desired cell type, i.e., directed differentiation or produce cells via transdifferentiation. Not only are the compositions and methods described herein useful for reprogramming cells, they are also applicable to this directed differentiation and transdifferentiation of cells to a desired phenotype. That is, the same technology described herein for reprogramming is directly applicable to the differentiation of the reprogrammed cell, or any other stem cell or precursor cell, for that matter, to a desired cell type.

In some embodiments of this aspect and all such aspects described herein, the synthetic, modified RNA molecule comprises at least two modified nucleosides. In one such embodiment, the two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2,N2,7-trimethylguanosine (m2,2,7G), and inosine (I). In one such embodiment of this aspect and all such aspects described herein, the at least two modified nucleosides are 5-methylcytidine (5mC) and pseudouridine (see e.g., Rossi US 2012/0046346, herein incorporated by reference).

Genes, proteins or RNA used in the methods of the invention include but are not limited to OCT4, SOX1, SOX 2, SOX 3, SOX15, SOX 18, NANOG, KLF1, KLF 2, KLF 4, KLF 5, NR5A2, c-MYC, 1-MYC, n-MYC, REM2, TERT, and LIN28.

It has also been shown that a single transcription factor may be employed in reprogramming adult fibroblasts to iPSCs with the addition of certain small molecule pathway inhibitors. Such pathway inhibitors include e.g., the transforming growth factor-beta (TGFb) pathway inhibitors, SB431542 (4-[4-(1,3-benzodioxol-5-yl)-5-(2-pyridinyl)-1H-imidazol-2-yl]-benzamide), and A-83-01 [3-(6-Methyl-2-pyridinyl)-N-phenyl-4-(4-quinolinyl)-1H-pyrazole-1-carbothioamide], the extracellular signal-regulated kinases (ERK) and microtubule-associated protein kinase (MAPK/ERK) pathway inhibitor PD0325901 (N-[(2R)-2,3-dihydroxypropoxy]-3,4-difluoro-2-[(2-fluoro-4-iodophenyl) amino]-benzamide), the GSK3 inhibitor CHIR99021 [6-((2-((4-(2,4-Dichlorophenyl)-5-(4-methyl-1H-imidazol-2-yl) pyrimidin-2-y1)amino)ethyl)amino)nicotinonitrile] which activates Wnt signaling by stabilizing beta-catenin, the lysine-specific demethylase1 Parnate (a/k/a tranylcypromine), the small molecule activator of 3'-phosphoinositide-dependent kinase-1 (PDK1) PS48 [(2Z)-5-(4-Chlorophenyl)-3-phenyl-2-pentenoic acid], the histone deacetylase (HDAC) inhibitors sodium butyrate and valproic acid, small molecules that modulate mitochondrial oxidation (e.g., 2,4-dinitrophenol), glycolytic metabolism (fructose 2,6-bisphosphate and oxalate), HIF pathway activation (N-oxaloylglycine and Quercetin) Zhu et al., 2010, *Cell Stem Cell* 7: 651-655, incorporated by reference herein it its entirety. Zhu et al showed that Oct4 combined with Parnate and CHIR99021 was sufficient to reprogram adult human epidermal keratinocytes.

Although individual protocols differ, a general reprogramming protocol consists of expanding differentiated adult cells from tissue samples, e.g., skin biopsies and contacting them with reprogramming factors as discussed above, e.g., infecting them, i.e., transfecting, with e.g., expression vectors, such as viral constructs containing transcripts for pluripotent transcription factors. The fibroblasts are obtained by art-known methods, e.g., by mechanically disrupting the tissue followed by enzymatic dissociation to release the fibroblasts, and culturing the fibroblasts by art-known methods, e.g., as described by Dimos et. al., 2008, Science Vol. 321 (5893): 1218-1221.

While illustrative aspects of the invention use vectors, e.g., viral vectors, in some aspects vectors are not required for transfection techniques, including those transferring mRNA molecules to cells.

Transfection of the fibroblasts with an expression vector is carried out according to instructions provided with the desired vector. After a time ranging from about 3 to about 7 days post-transfection, the cells are dissociated and contacted with fluorescent tagged antibodies raised against the CD13$^{NEG}$, SSEA4$^{POS}$ and Tra-1-60$^{POS}$ surface markers. The dissociated and antibody-labeled cells are then resuspended in a phosphate buffered saline solution and moved to an automated sorting and isolation of iPSC clones. Surface marker positive cells are sorted by tag color or absence thereof directly into sterile tubes containing tissue culture media or multiwell (6-96 well) tissue culture plates coated with MEFs or cell free biological matrices and cultured until formation of visible colonies occurs.

Colonies are then further confirmed as iPSC by light microscopic inspection of the resulting clones or optionally by microscopic fluorescence inspection of clones labeled with fluorescent tagged antibodies. Optionally, in certain embodiments, one or more of the vectors also insert a green fluorescence protein (GFP) expression marker, for convenience in sorting and identification. Several individual colonies possessing morphological characteristics consistent with pluripotent ES cell lines are plucked from cultures and expanded individually to form monoclonal cultures.

In one preferred embodiment of the inventive system, the treated cells are subjected to genetic analysis to provide early confirmation and identification of iPSCs. Preferably, the genetic analysis is conducted by Southern blot, but other art-known methods may be employed which include but are not limited to MicroArray, NanoString, quantitative real time PCR (qPCR), immunofluorescence microscopy, flow cytometry. Detection of enzymatic activity of alkaline phosphatase, positive expression of the cell membrane surface markers SSEA3, SSEA4, Tra-1-60, Tra-1-81 and the expression of the KLF4, Oct3/4, Nanog, Sox2 transcription factors in reprogrammed human fibroblasts confirms that a clone is an iPSC. Preferably, all of the markers are present.

Any art-known transfection vector may be employed as a reprogramming factor, including, e.g., an RNA such as mRNA, microRNA, siRNA, antisense RNA and combinations thereof. Other expression vectors that may be employed include, e.g., a retrovirus, a lentivirus, an adenovirus, an adeno associated virus, a herpes virus, a Sindbis virus, a pox virus, a bacula virus, a bacterial phage, a Sendai virus and combinations thereof. Preferably, an employed vector is a non-replicative vector such as, e.g., Sendai virus vectors engineered to be nonreplicative. The preferred Sendai virus vector, while incapable of replication, remains capable of productive expression of nucleic acids encoding protein(s) carried by the vector, thereby preventing any potential uncontrolled spread to other cells or within the body of a vaccinee. This type of Sendai vector is commercially available as a CytoTune™-iPSC Sendai viral vector kit (DNAVEC, DV-0301).

Any art-known transfection method may be employed to insert such vectors into the adult fibroblasts, including, e.g., electroporation, gene gun, and the like. Chemical transfection is optionally conducted by means of a transfecting agent e.g., a polymer, calcium phosphate, a cationic lipid, e.g., for lipofection, and the like. Cell penetrating peptides are also optionally employed to carry vectors or other agents into the adult fibroblast cells. In brief, cell-penetrating peptides include those derived from proteins, e.g., protein transduction domains and/or amphipathic peptides that can carry vectors or other agents into the cell include peptides. The subject of cell-penetrating peptides has been reviewed, e.g., by Heitz et al., 2009 British Journal of Pharmacology, 157: 195-206, incorporated by reference herein in its entirety. Other cell penetrating peptides are art-known, and are disclosed by Heitz, Id. Other cell-penetrating technologies including, e.g., liposomes and nanoparticles, are also contemplated to be employed in the methods of the present invention. Liposomes and nanoparticles are also described by Heitz, Id.

Antibodies can be employed in order to identify the transformed cells. Four antibodies against stem cell specific surface proteins are commonly used to identify and characterize human pluripotent stem cell populations; SSEA3, SSEA4, Tra-1-60 and Tra-1-81. The Stage Specific Embryonic Antigens 3 and 4 (SSEA3 and SSEA4) are two monoclonal antibodies which recognize sequential regions of a ganglioside present on human 2102Ep cells (Henderson et al., 2002 Stem Cells 20: 329-337; Kannagi et al., 1983, Embo J 2: 2355-2361). The Tra-1-60 and Tra-1-81 antibodies were originally raised against human embryonal carcinoma (EC) cells (P W et al., 1984, Hybridoma 3: 347-361) and have been shown to specifically recognize a carbohydrate epitope on a keratan sulfated glycoprotein identified as podocalyxin, a member of the CD34-related family of sialomucins (Badcock et al., 1999, Cancer Research 59: 4715-4719; Nielsen et al., 2007, PLoS ONE 2: e237; Schopperle and DeWolf, 2007, Stem Cells 25: 723-730). Several other surface markers have been shown to be expressed on ES cells and include CD326 or EpCam (Sundberg et al., 2009, Stem Cell Res 2: 113-124), CD24 (Heat Stable Antigen) and CD133 (Barraud et al., 2007, Journal of Neuroscience Research 85, 250-259) (Gang et al., 2007, Blood 109: 1743-1751). Chan et al., 2009, Id. reported that the identification of bona fide IPSc from fibroblasts undergoing reprogramming via four factor retro viral transduction can be achieved via live cell imaging and by the observation, over time, that fibroblasts lose expression of the cell surface markers CD13 and D7Fib, and gain expression of the pluripotent stem cell markers SSEA4 and Tra-1-60 (Chan et al., 2009, Id.).

Also contemplated to be within the scope of the invention are compositions comprising iPSCs, e.g., compositions employed as research tools, or as pharmaceutical compositions, comprising effective amounts of iPSCs prepared by the inventive automated system.

The invention further relates to treating a disease or disorder in an animal or person in need thereof by administering the iPSCs, e.g., methods of treatment and/or tissue/organ repair by administering iPSCs produced by the inventive automated system, or differentiated cells derived therefrom. Appropriate differentiated cells (of ectodermal, mesodermal or endodermal lineage) may be derived from iPSCs produced by the inventive methods. The mode of administration can be determined by a person of skill in the art depending on the type of organ/injury to be treated. For example, iPSCs or differentiated cells derived therefrom, may be administered by injection (as a suspension) or implanted on a biodegradable matrix.

In addition, the invention relates to methods of testing pharmaceuticals by contacting iPSCs, transdifferentiated, or differentiated cells derived therefrom, for example, with one or more pharmaceutical agents of interest, and then detecting the effect of the applied pharmaceutical agent(s) on the contacted cells. For efficiency, pharmaceutical agent(s) are applied to a battery of iPSCs, or differentiated cells derived therefrom. The cells can vary in tissue source, in differentiated cell type, or allelic source, to allow identification of cells or tissue types that react favorably or unfavorably to one or more pharmaceutical agents of interest.

Further, the iPSCs produced by the inventive automated system may be used as a vehicle for introducing genes to correct genetic defects, such as osteogenesis imperfecta, diabetes mellitus, neurodegenerative diseases such as, for instance, Alzheimer's disease, Parkinson's disease, the various motor neuron diseases (MND), e.g., amyotrophic lateral sclerosis (ALS), primary lateral sclerosis (PLS), progressive muscular atrophy (PMA) and the like.

iPSCs produced by the inventive automated system may also be employed to provide specific cell types for biomedical research, as well as directly, or as precursors, to produce specific cell types for cell-based assays, e.g., for cell toxicity studies (to determine the effect of test compounds on cell toxicity), to determine teratogenic or carcinogenic effects of test compounds by treating the cells with the compound and observing and/or recording the compound's effects on the cells, e.g., effect on cellular differentiation.

The present invention may be better understood by reference to the following non-limiting Examples. The following examples are presented in order to more fully illustrate the preferred embodiments of the invention. They should in no way be construed, however, as limiting the broad scope of the invention.

Example 1

Figure 5A:
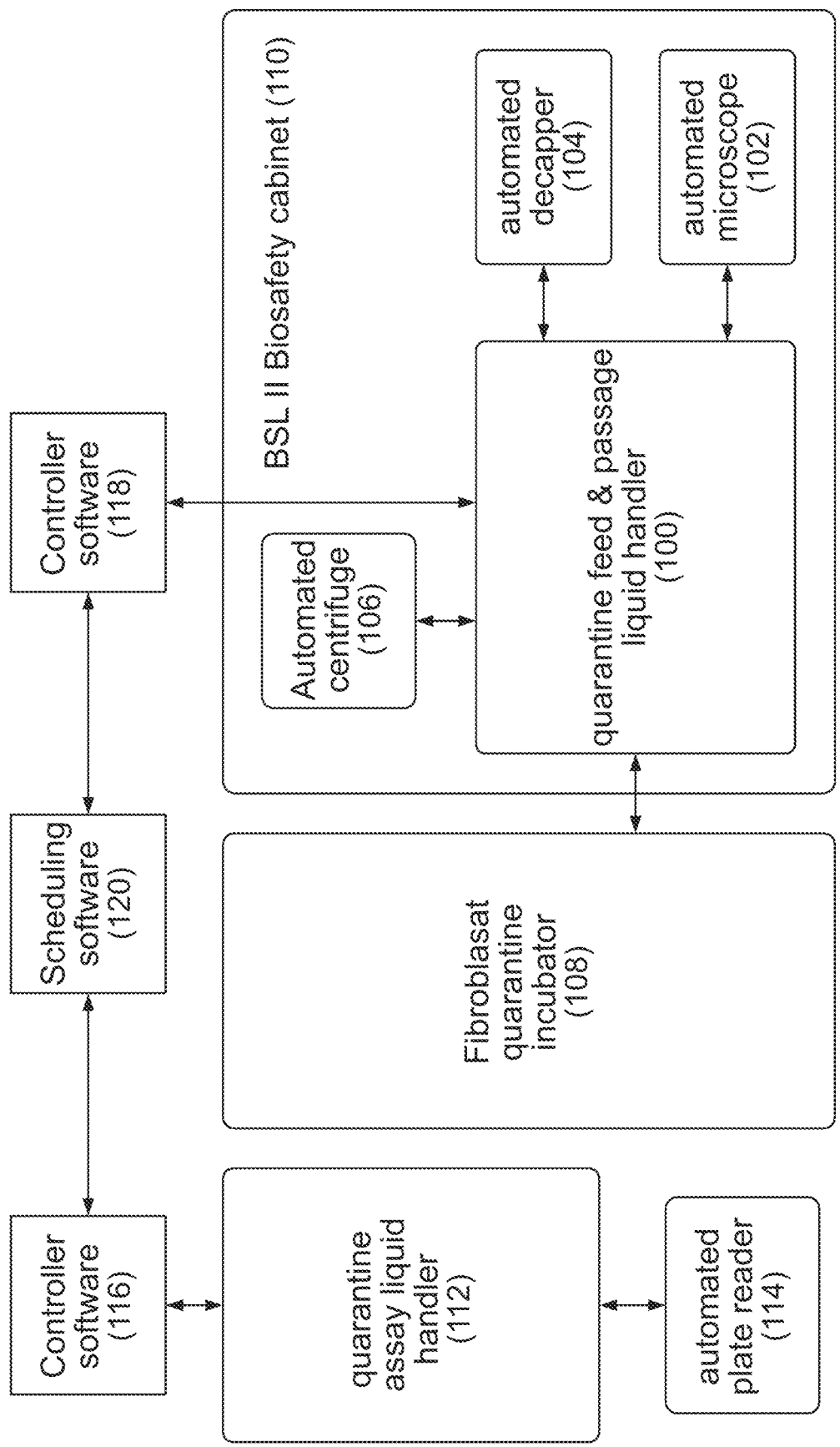
FIGS. 5A-5C show an example of an equipment configuration to accomplish the workflow.
Figure 5B:
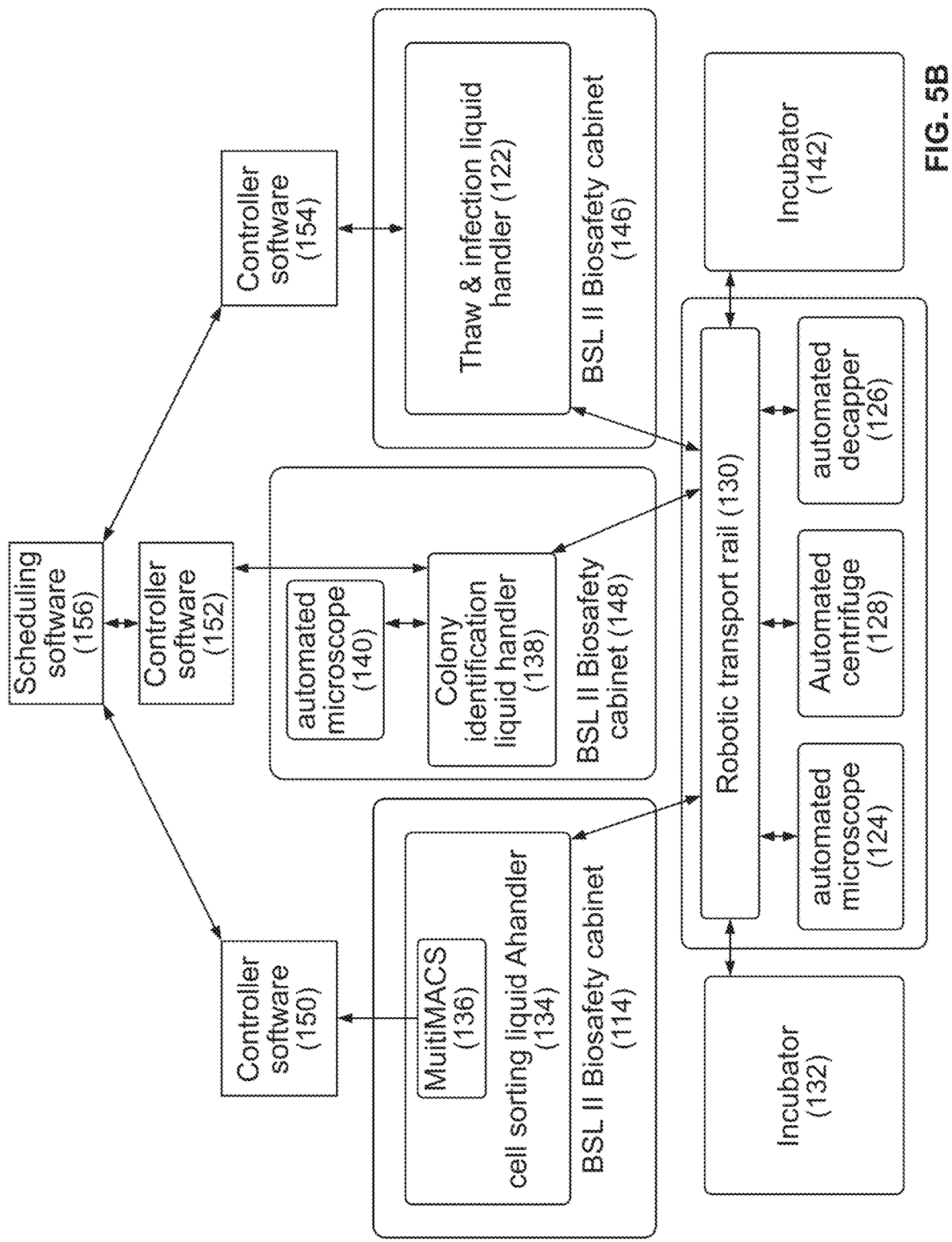
Figure 5C:
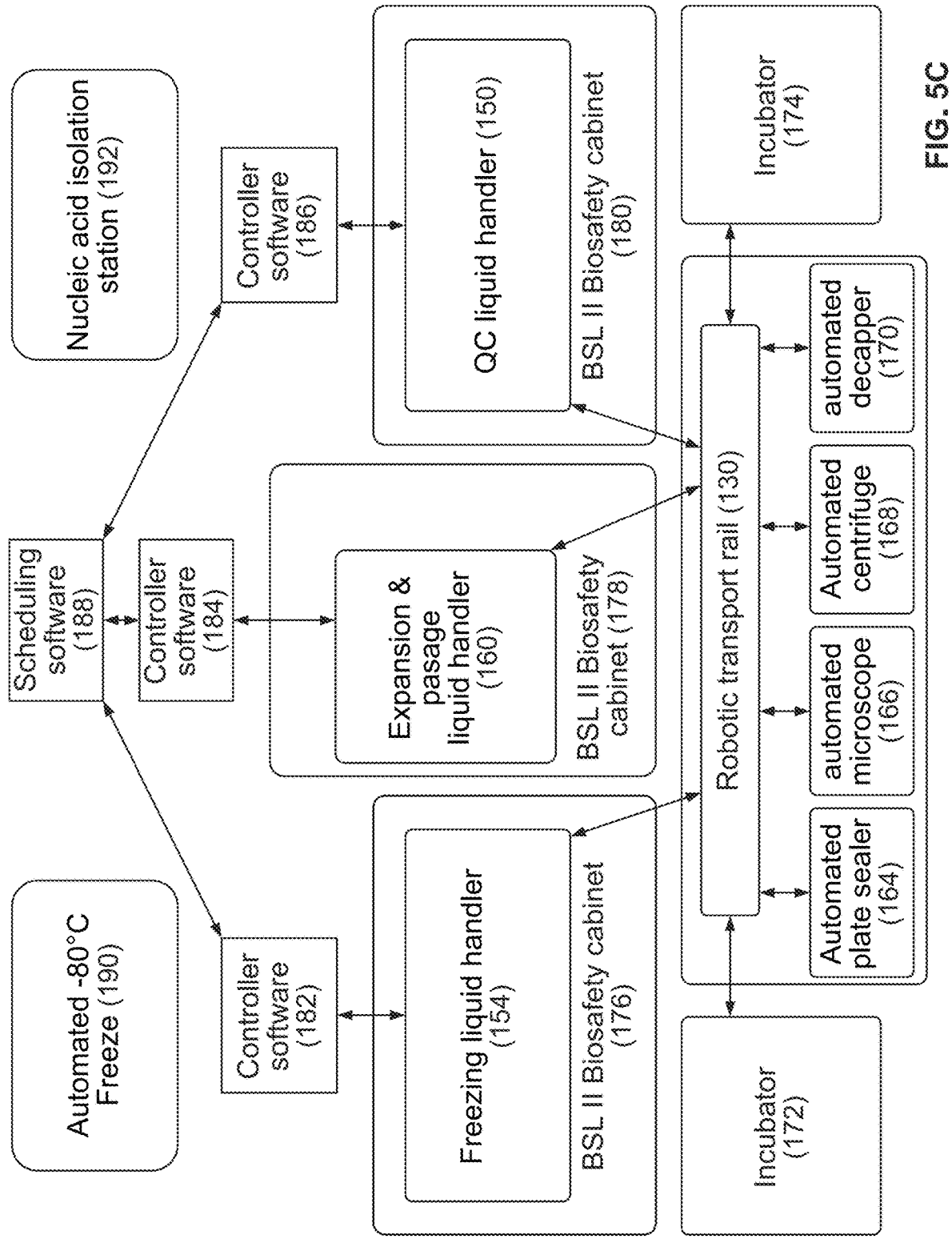

FIGS. 5A, 5B and 5C illustrate an example of the equipment configuration needed to accomplish the workflow. FIG. 5A shows a system configuration for the automated expansion and quality control of a fibroblast bank. FIG. 5B shows a system configuration for the automated thawing of patient samples, such as fibroblasts, automated introduction of reprogramming factors with the patient samples, such as fibroblasts, automated cell sorting with MultiMACS, and automated colony identification and reformatting. FIG. 5C shows a system configuration for the automated expansion of iPS clones, automated Embryoid Body production, and automated freezing.

Automated Derivation of a Fibroblast Cell Bank

As an example, the hardware configuration used to accomplish the derivation of a fibroblast bank consists of a Hamilton STARlet liquid handling robot (100) connected to the following hardware components: a Cytomat 24C GLS automated incubator (108) that allows for the incubation of cell cultures, a Cyntellect Celigo cytometer (102) for automated image acquisition and analysis, an Agilent V-Spin automated centrifuge (106) for the centrifugation of cells in plates or tubes, and a Hamilton Capper DeCapper (104) for the automated capping and decapping of cryotubes. These components are further controlled by programmable software (118) on a PC that communicates with all instruments and controls the manipulation of cell culture-ware and cells among the hardware components. The controller software further communicates with scheduling software (120) to link System interactions. The Hamilton STARlet (100) is equipped with a Modular Arm for 4/8/12 channel pipetting, 8 pipetting channels, iSWAP plate handler, CO-RE Gripper for plate and lid handling, MultiFlex tilt Module for tilting plates during media exchanges, Hamilton Heated Shaker 2.0, as well as a Carrier Package for flexible layout of the liquid handling platform with plate and lid parks, pipette stackers, daughter plate stackers and troughs for holding media. The Cyntellect Celigo (102) is comprised of an imaging unit and programmable software on a PC for control of image acquisition and image analysis. The Celigo is preferred because it does not move the cell culture plates during imaging thereby reducing agitation of plated biopsies. The Hamilton Capper Decapper (104) and the Agilent V-Spin centrifuge (106) are contained with the Hamilton STARlet within a NuAire BSL II biosafety cabinet (110) to maintain a sterile operating environment during manipulation of cell culture plates.

To control plate handling on the automated system, MICROLAB STAR VENUS TWO Base Pack 4.3 software (118) with VENUS Dynamic Scheduler 5.1 (120) are used in conjunction with individual attached hardware component drivers for the centrifuge (106), Capper Decapper (104), Celigo (102), and Cytomat 24 (108) and Cytomat transfer station to integrate the operation of the system. The following methods programmed using the provided controller software (118) are needed for functionality of the system and can be combined in defined sequence to accomplish the derivation of fibroblast lines from patient skin biopsies:

1. Load 6-well biopsy plates (22, 24) onto the STARlet (100) and transfer to the Cytomat incubator (108).
2. Confluency check (26, 28) on Celigo (102) and a media exchange on the STARlet (100).
3. Confluency check (28) on Celigo (102).
4. Media change (30) on the STARlet (100) for full media exchange.
5. Assay plate preparation (34) on STARlet (100) and Agilent V-Spin centrifuge (106).
6. Passaging (44) on the STARlet (100).
7. Passage and cherry pick (42) on the STARlet (100).
8. Passage, harvest and freeze on the STARlet (100).
9. Retrieve plates (46, 40) onto the STARlet (100) from the Cytomat (108).

Automated *Mycoplasma* Testing on Quarantine Assay System

An independent hardware configuration is used to accomplish the mycoplasma testing of a fibroblast bank and consists of a Hamilton STARlet liquid handling robot (112) connected to a BioTek Synergy HT Reader (114). These components are further controlled by programmable software (116) on a PC that communicates with all instruments and controls the manipulation of cell culture-ware and cells between the hardware components. The Hamilton STARlet (112) is equipped with a Modular Arm for 4/8/12 channel pipetting, 8 pipetting channels, iSWAP plate handler, CO-RE Gripper for plate and lid handling, as well as a Carrier Package for flexible layout of the liquid handling platform with plate and lid parks, pipette stackers, daughter plate stackers and plate parks and troughs for holding reagents needed for the assay.

To control plate handling on the automated system, MICROLAB STAR VENUS TWO Base Pack 4.3 software (116) is used in conjunction with the attached hardware component drivers for the BioTek Synergy HT Reader (114) to integrate the operation of the system. A method is programmed using this software that allows execution of the MycoAlert *Mycoplasma* Detection assay (36) and data analysis to determine assay result (38).

Automated System for Thawing, Infection, and Identification of Reprogrammed Cells The hardware configuration needed to thaw fibroblasts, infect fibroblasts with reprogramming viruses, magnetic sort of reprogrammed cells, and identification of stem cell colonies is composed of three Hamilton STAR liquid handling units (122, 136, 138), two Cytomat 48C incubators (132), one Cytomat 2C 425 incubator (142), two Cyntellect Celigo cytometers (124, 140), Hamilton Capper DeCapper (126), Agilent V-Spin (128), Miltenyi MultiMACS magnetic separation device (136). The liquid handlers, a Celigo, the Hamilton Capper Decapper and Agilent V-Spin are all connected by a Hamilton Rack Runner robotic rail (130). Each Hamilton STAR is equipped with a Modular Arm for 4/8/12 channel pipetting, 8 pipetting channels, iSWAP plate handler, CO-RE Gripper for plate and lid handling, one or more MultiFlex tilt Module for tilting plates during media exchanges, one or more Hamilton Heated Shaker 2.0, as well as carrier packages for flexible layout of the liquid handling platform with plate and lid parks, pipette stackers, daughter plate stackers and troughs for holding media. One of the Hamilton STAR liquid handlers (122) is also equipped with a 96-well pipetting head. One Celigo (140) and the Cytomat 2C incubator (142) are connected directly to one of the Hamilton STARs (138) to facilitate automated cell sorting. The Hamilton STARs are contained within NuAire BSL II biosafety cabinets (144, 146, 148) to maintain a sterile operating environment during manipulation of cell culture plates. The remaining components are enclosed in a Hepa filtered hood to maintain a sterile operating environment during transportation of cell culture plates among the devices. The Cytomat 48C incubator (132) is connected to the other components of the system by the Rack Runner transport rail (130).

To control plate handling on the automated system, MICROLAB STAR VENUS TWO Base Pack 4.3 software controllers (150, 152, 154) with VENUS Dynamic Scheduler 5.1 (156) are used in conjunction with individual attached hardware component drivers for all of the Hamilton STARs (122, 134, 138), the centrifuge (128), the Capper/decapper (126), the two Celigos (140, 124), the Rack Runner (130), and Cytomat 24 (132), the Cytomat 2C (142) and associated Cytomat transfer stations to integrate the operation of the system. The following methods programmed using the provided controller software (150, 152, 154) are needed for functionality of the system and can be combined in a defined sequence to accomplish derivation of iPS colonies from fibroblasts:

1. Load mycoplasma free 6-well biopsy plates (48) onto the STAR (122) and transfer to the Cytomat incubator (132) under clean growth conditions (60).
2. Confluency check (50) on Celigo (124) and a media exchange on the STAR (122).
3. Passage, harvest (52) and freeze (54, 56) on the STAR (122).
4. A thawing method whereby cryotubes containing fibroblasts (61) are loaded and thawed on the STAR (122), followed by decapping of tubes (126) and washing of fibroblast, followed by resuspending cells in plating media and plating fibroblasts on 6 well plates (62) and transferring to Cytomat incubator (132).
5. Media change on the STARlet (122) for full media exchange.
6. Confluency check on Celigo (124).
7. Passaging and seeding of fibroblasts in 24-well plates (64) on the STARlet (122).
8. A method for infection of fibroblasts (64) on the STARlet (122).
9. A method to add a defined volume of media to wells on STAR (122, 138, 144).
10. A method for executing a half media exchange on STAR (122, 138, 144).
11. A method for magnetic sorting, dilution and plating (66) on the STAR (144) attached to the Miltenyi MultiMACS (136) and Celigo (124).
12. A method for a three quarter media exchange on the STAR (122, 138, 144).
13. A method for a executing an immunocytochemical stain on live colonies followed by automated imaging of the colonies (66) using a STAR (138) and Celigo (140).
14. A method for harvesting, cherry picking and replating colonies (68) from selected wells on a STAR (138).
15. Retrieve plates onto the STARlet (122, 138, 144) from the Cytomat (132).

Automated System for Expansion, Quality Control, and Freezing of Reprogrammed Cells The hardware configuration needed to expand reprogrammed Stem Cell Colonies, generate plates of colonies for quality control assays and generate plates and tubes for cryostorage is composed of three Hamilton STAR liquid handling units (150, 154, 160), Cytomat 24C incubator (172), one Cytomat 2C 425 incubator (174), one Cyntellect Celigo cytometer (166), Hamilton Capper DeCapper (170), Agilent V-Spin (168), and Agilent PlateLoc plate sealer (164). The liquid handlers, a Celigo, the Hamilton Capper Decapper, Agilent V-Spin, and Agilent PlateLoc plate sealer are all connected by a Hamilton Rack Runner robotic rail (162). The Hamilton STARs and STARlet are equipped with Modular Arms for 4/8/12 channel pipetting, 8 pipetting channels, iSWAP plate handlers, CO-RE Grippers for plate and lid handling, one or more MultiFlex tilt Modules for tilting plates during media exchanges, one or more Hamilton Heated Shaker 2.0 s, as well as a carrier packages for flexible layout of the liquid handling platforms with plate and lid parks, pipette stackers, daughter plate stackers and troughs for holding media. One of the STARs (160) also has a 96 channel Multichannel pipetting head to facilitate media exchanges and passaging. The Cytomat 2C and Cytomat 24C incubators are connected to the Hamilton STARs by a Hamilton Rack Runner transport rail (162) to facilitate automated media exchanges. The Hamilton STARs are contained within a NuAire BSL II biosafety cabinet (176, 178, 180) to maintain a sterile operating environment during manipulation of cell culture plates. The remaining components are enclosed in a Hepa filtered hood to maintain a sterile operating environment during transportation of cell culture plates among the devices.

To control plate handling on the automated system, MICROLAB STAR VENUS TWO Base Pack 4.3 software controllers (182, 184, 186) with VENUS Dynamic Scheduler 5.1 (188) are used in conjunction with individual attached hardware component drivers for the centrifuge, decapper, plate sealer, Celigo, and Cytomat incubators and Cytomat transfer station to integrate the operation of the system. The following methods are needed for functionality of the system and can be combined in a defined sequence to expand cell cultures in plates for quality control assays and freezing in plates or cryovials:

1. A loading method on the STAR (160) to receive plates (68) from the previous stage into the Cytomat incubator (172).
2. Media change on the STAR (150, 154, 160) for full media exchanges using tilt modules and 8-channel pipetting arms.
3. Confluency check on Celigo (166) with associated methods to transport plates to and from the STARs (150, 154, 160) and Cytomat incubator (172).
4. A method for passaging and seeding of iPSCs in 96-well plates (68-90) on the STARs (150, 154, 160).
5. A method for executing a partial media exchanges on the STARs (150, 154, 160).
6. A method for harvesting, cherry picking and replating colonies from selected 96-well wells to new 96-well plates (80, 82, 86, 88) on a STAR (150, 154, 160).
7. A method for harvesting, cherry picking and replating colonies from selected 96-well wells to new 24-well plates (90, 92) on a STAR (154).
8. A method for harvesting and cherry picking and replating colonies from selected 24-well wells to new 6-well plates (92, 94) on a STAR (154).
9. Passage, harvest and distribute cells in freezing plates (88) on the STAR (154).
10. Passage, harvest and distribute cells in cryotubes (96) on the STAR (154).
11. Retrieve plates onto the STARs (150, 154, 160) from the Cytomat 24C (172) or Cytomat 2C (174).

Example 2

Production of a Fibroblast Bank for Reprogramming

The first step in the workflow to derive iPSCs from patient samples is to obtain and expand adult cells. This is accomplished, for example, by obtaining a skin punch biopsy or discarded dermal tissue, then isolating and expanding cultures of fibroblasts from the tissue. In our workflow, this is accomplished by the automated system comprised of Systems 1 and 2. The automated components of System 1 and 2 (100-120) and System 3 (122-132, 154, 190) perform the steps needed to derive a fibroblast bank stored in cryotubes (61) from patient samples, including plating of a patient biopsy (2, 22-24), outgrowth and passaging (4, 26-32) (rolling production on liquid handling robot), QC (6, 34-46) (automated testing for mycoplasma), and automated freezing on the liquid handling robot (8, 48-56). For example, the workflow and decision tree for production of fibroblasts from biopsies is divided into Quarantine (58) and Clean phases (60). As biopsies enter the facility, a technician plates biopsies in 6-well plates (22) and logs the plates into the automated incubator (24) to begin the quarantine workflow. After biopsies are given time to attach to the plate, the liquid handling robot retrieves the plates from the automated incubator to feed and check confluency of the outgrowth of adult fibroblasts from the plated tissue on an automated microscope (26). The plates are returned to the incubator and allowed to continue to outgrow (28). The liquid handler removes the plate from the incubator and exchanges the media for antibiotic and antimycotic free media (30) to prepare for mycoplasma testing. The robot moves the plate to the incubator for another five days (32). The robot then removes the plate and retrieves media to daughter plates for mycoplasma test (34). The daughter plates are moved to the Quarantine Assay system for mycoplasma testing (36). A choice is then made based on a positive signal from the assay (38). If all wells of a 6-well plate fail with a positive assay result (40) they are discarded. If all wells of a 6-well plate are negative and free of mycoplasma, they are transferred out of quarantine into the clean growth environment provided by Systems 3, 4, 5 (46). If some wells are positive and some wells are negative, the negative wells are maintained in quarantine (42). The negative wells are passaged (44) to new plates, transferred to the incubator, and the source plates containing positive wells are discarded. These cultures proceed through steps to retest for mycoplasma (24-38). Clean cultures are monitored for growth (50), passaged (52) and frozen in cryovials (54, 56, 61).

Production of Stem Cell Arrays

To produce iPSCs, Fibroblasts in cryotubes (61) are plated by the automated system (10), reprogramming factors are introduced by the automated system (12), iPSCs are isolated by automated sorting and isolation in System (14), desired clones are selected by the automated system (16), and expanded by the automated system (16), automated quality checks by the automated system (QC) for pluripotent status by marker assays and embryoid body assays (18), followed by automated freezing and storage of desired cells by the automated system (20). These steps are accomplished on the automated systems 3, 4, 5, 6, 7, and 8 (122-192).

For example, the automated iPS derivation process begins when 96 patient and control fibroblast samples in cryotubes (61) are plated in individual wells of a 6-well plate (62). These are passaged at defined cell number into individual wells of a 24-well plate for infection using viruses encoding reprogramming factors (64). In the next step, reprogrammed samples are depleted of non-reprogrammed cells by cell sorting or magnetic bead-based enrichment and plated at clonal density in multiple wells in 96-well plates (66). In this example, 6 wells (66) are identified containing a single clone positive for a pluripotency surface marker. These clones are cherry picked and consolidated into a minimum number of 96-well plates (68). These clones are serially passaged until confluence within a well is achieved for each starting sample (72). Each plates' samples are then replicated onto duplicate plates (74, 76), one plate for a Pluripotency quality control assay needed to determine pluripotent status of the individual clones (74) and one plate for carrying forward in subsequent passages (76). The plate that is carried forward is passaged again into three plates (78, 80, 82). One plate is harvested for QC assay that assesses Karyotype and genetic diversity (78), one plate (82) is passaged onto v-bottom plates to form embryoid bodies (84) for a QC assay that assesses differentiation capability of the iPS clones, and the final plate (80) is carried forward for further expansion. Individual clones that do not pass quality control from previous pluripotency QC assays are not carried forward as indicated by "X" in the wells in FIGS. 4B2 and 4C (80, 82, 90). Remaining clones are consolidated onto as few plates as possible until one to three clones remain (86). These clones are expanded for cryopreservation while attached to the plate (88) or further expanded (92, 94) and cryopreserved in cryovials (96).

Embryonic stem cells (ES) are also contemplated to be used with the automated system of the invention to generate differentiated adult cells. ES cells are derived from the blastocyst of an early stage embryo and have the potential to develop into endoderm, ectoderm, and mesoderm (the three germ layers) (i.e., they are "pluripotent"). In vitro, ES cells tend to spontaneously differentiate into various types of tissues, and the control of their direction of differentiation can be challenging. However, some progress has been achieved in the directed differentiation of ES cells to particular types of differentiated daughter cells. For example, it is now possible to direct the differentiation of human ES cells to functional midbrain dopaminergic neurons using defined factors added to the cell cultures at defined stages of their stepwise differentiation (see, e.g., Kriks et al., 2011 Nature, November 6. doi: 10.1038/nature10648 (Epub)). As differentiation is not homogenous, it remains necessary to isolate populations of interest for further study or manipulation. The process and instrumentation described here could be used to first derive and expand pluripotent embryonic stem cells and also isolate subpopulations of their differentiated derivatives by automated methods including automated magnetic cell isolation.

For example, whole human blastocysts can be plated on matrices in multi-well plates amenable to the automated process. Outgrowths from these plated blastocysts could be isolated using the same automated magnetic isolation procedures performed by the robotic instrumentation and methods described for the isolation of induced pluripotent stem cells. The resulting human embryonic stem cell lines could be expanded, selected by quality control assays and frozen using the same automated procedures described herein.

Further, using pluripotent stem cells, either blastocyst derived or induced by defined factors or by somatic cell nuclear transfer, differentiated derivatives can be isolated using the described workflow and instrumentation. The differentiated derivatives can be obtained by directed application of defined factors required to induce a cell fate change or after spontaneous differentiation. For example, inhibitors of the TGF beta pathway can be used to induce neural cell fates from pluripotent stem cells. Neural cells can be subsequently isolated from non-neural by magnetic bead immunolabeling of surface antigens, such as NCAM. The described workflow and instrumentation can be used to magnetically isolate, select, culture and expand differentiated cells like neurons. This process is also applicable to other differentiated cell types, like cardiac cells, for which there exist antibodies that recognize cell surface antigens specific to the cell type of interest.

Multipotent stems cells are also contemplated to be used with the automated systems of the invention to generate differentiated adult cells. In particular, mesenchymal stem (MS) cells can be employed to generate differentiated adult cells using the automated systems of the invention. MS cells are the formative pluripotent blast or embryonic-like cells found in bone marrow, blood, dermis, and periosteum and placenta that are capable of differentiating into specific types of mesenchymal or connective tissues including adipose, osseous, cartilaginous, elastic, muscular, and fibrous connective tissues. The specific differentiation pathway which these cells enter depends upon various influences from mechanical influences and/or endogenous bioactive factors, such as growth factors, cytokines, and/or local microenvironmental conditions established by host tissues. Examples include differentiation of MS cells into differentiated cells with the properties of chondrocytes for cartilage repair, e.g., see U.S. Pat. No. 8,048,673.

Chromosomal Testing

In some aspects, the Nanostring nCounter Plex2 Assay Kit is used to target the 400 genomic loci allows for integrated molecular karyotype analysis coupled with "fingerprint" tracking of cell line identity. The molecular karyotype analysis utilizes an average of 8 probes per chromosome arm to verify genomic stability during the course of cell culture derivation and expansion of iPSC lines. Identity analysis will also be performed on all lines based on 30 common copy number variations (CNVs) of polymorphic loci, which allows for unambiguous identification of individual genomes.

Pluripotency Analysis

In one aspect, surface marker staining is performed to show that cells are positive for Tra-1-60 surface marker, which is monitored e.g., with the Celigo automated imager. PSC lines must show a significant level of the pluripotency genes. In one example, we utilize a probe set of 100 gene makers (described below) that includes the six markers for pluripotency (Oct4, Klf4, cMyc, Nanog, Lin28, ZFP42, and Sox2). To perform this analysis we lyse a sample of cells and harvest RNA. We utilize the nCounter Plex2 Assay Kit to analyze expression levels in multiple samples and hundreds of gene targets simultaneously enabling the high-throughput approach to PSC characterization. As the nCounter gene expression assays are quantitative, selection criteria is based on expression levels falling within a range relative to a control panel of established hESC lines analyzed grown under identical conditions. Lines that pass pluripotency gene expression criteria will be further expanded and differentiated in vitro in embryoid body (EB) assays.

EB Formation Gene Expression Assay

It has been shown that epigenetic and transcriptional variation is common among human pluripotent cell lines and that this variation can have significant impact on a cell line's utility. In an illustrative example, the panels of gene markers includes:

83 different gene markers selected from each of the 3 germ layers (83)
 5 retrovirus transgene (4 factors with single detection probe, 1 probe)
 5 sendai transgenes (4 factors+vector only, 5) Oct4, Klf4, cMyc, Nanog, Lin28, ZFP42 (pluripotency, Sox2 is in germlayer group, 6 probes) Sex markers SRY, XIST (2)—donor sex must match or lines will be rejected.
 Housekeeping genes, ACTB, POLR2A, ALAS1 (3 probes).
 hPSC line expansion and storage.

Automated Expansion

Cell lines are expanded through plating of the initial cells into 2 separate wells of a 6-well plates then placing them within a CO2 incubator and allowing them to grow up to a maximum of 95% confluence.

Storage

The vials are first placed within the SAM −80 freezer to perform the initial slow cool. This system has automated monitoring of temperature and logs of time the system is accessed.

Next, the vials are placed in LN2 for long-term storage. Quality control for monitoring is detailed later in this proposal. Each vial is individually marked with a unique 2D barcode and inventory is tracked within the LIMS.

hPSC Line Characterization iPSC and EB gene expression analysis-Set of probes covering lineage differentiation assay scorecard (100 genes) to monitor germ layer differentiation in EB assays, pluripotency markers, sex markers and transgene expression.

Freeze-Thaw Analysis

Cells are counted following recovery and plated in one well of a 6-well plate. Colonies are photographed on the first day of appearance and then 5 days later, colonies must display a doubling time no larger than 36 hours.

Surface Marker Analysis

Perform surface marker analysis using automated system using high content imaging of Tra-1-60 staining using the Celigo automated imager.

iPSC and EB Gene Expression Analysis

Pluripotency gene expression—iPSC clones must show a significant level of the pluripotency genes. We utilize a probe set of 100 gene makers (described below) that includes the six markers for pluripotency (Oct4, Klf4, cMyc, Nanog, Lin28, ZFP42, and Sox2). To perform this analysis we lyse a sample of cells for each of the selected clones and harvest RNA. We utilize the nCounter Plex2 Assay Kit to analyze expression levels in multiple samples and hundreds of gene targets simultaneously enabling the high-throughput approach to iPSC characterization. As the nCounter gene expression assays are quantitative, selection criteria is based on expression levels falling within a range relative to a control panel of established hESC lines analyzed grown under identical conditions. Selected clones that pass pluripotency gene expression criteria will be further expanded and differentiated in vitro in embryoid body assays.

EB Formation Gene Expression Assay

In order to firmly establish the nature and magnitude of epigenetic variation that exists among human pluripotent stem cell lines, three genomic assays were applied to 20 established embryonic stem cell (ESC) lines and 12 iPSC lines that were recently derived and functionally characterized. As a step toward lowering the experimental burden of comprehensive cell line characterization, and to improve the accuracy over standard existing assays, all of the data from these studies are combined using the three genomic assays into a bioinformatics scorecard, which enables high-throughput prediction of the quality and utility of any pluripotent cell line. We utilize this scorecard to analyze gene expression data from the EBs formed from each clone of our iPSC lines. To test differentiation potential, we use the automated system to generate EBs in 96-well v-bottom plates and ends in RNA harvest for Nanostring nCounter Plex2 Assay Kit. 83 different gene markers selected from each of the 3 germ layers (83):

5 retrovirus transgene (4 factors with single detection probe, 1 probe)
  5 sendai transgenes (4 factors+vector only, 5)
  Oct4, Klf4, cMyc, Nanog, Lin28, ZFP42 (pluripotency, Sox2 is in germlayer group, 6 probes)
  Sex markers SRY, XIST (2)
  Housekeeping genes, ACTB, POLR2A, ALAS1 (3 probes).

Karyotype and Identity Analysis

Prior to accepting a line and at the end of each expansion, we utilize the Nanostring nCounter Plex2 Assay Kit to target the 400 genomic loci allowed for integrated molecular karyotype analysis coupled with "fingerprint" tracking of cell line identity. The molecular karyotype analysis utilizes an average of 8 probes per chromosome arm to verify genomic stability during the course of cell culture derivation and expansion of iPSC lines. The "fingerprint" identity tracking analysis will rely on a combinatorial signature based on 30 common copy number variations (CNVs) of polymorphic loci, which allows for unambiguous identification of individual genomes. Additionally to avoid misidentification, tissue donors known to be relatives will not be processed in the same batch, as it is theoretically possible they will have similar CNVs. The data from the identity analysis will be cross-referenced with the initial CNV data to ensure that our LIMS system properly tracked all cell lines.

Freeze-Thaw Analysis

Freeze-Thaw Analysis: one vial is thawed after cryopreservation. Cells are counted following recovery and plated in one well of a 6-well plate. Cultures are observed daily. Colonies are photographed on the first day of appearance and then 5 days later. Colonies must at least double in diameter within 5 days after first observation.

Figure 6A:
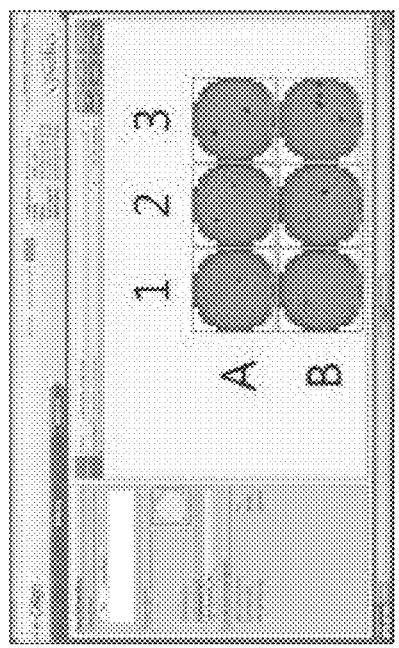
FIGS. 6A-6D show the automated biopsy outgrowth tracking system.
Figure 6B:
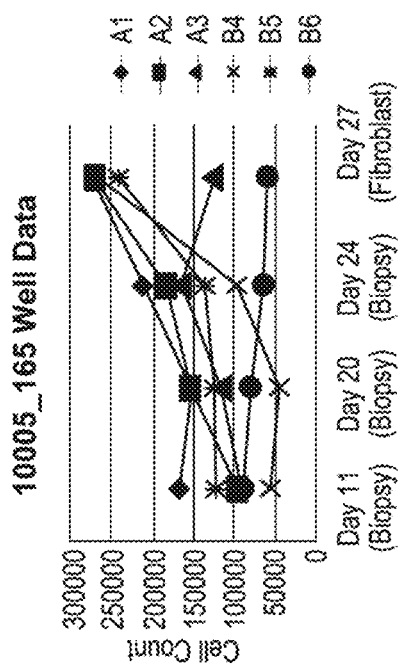
Figure 6C:
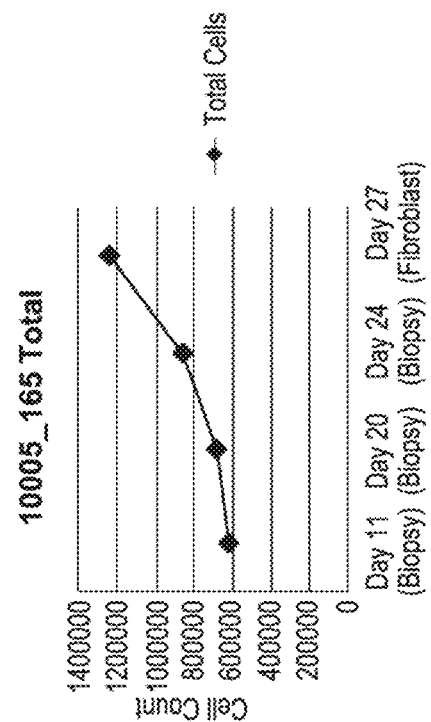
Figure 6D:
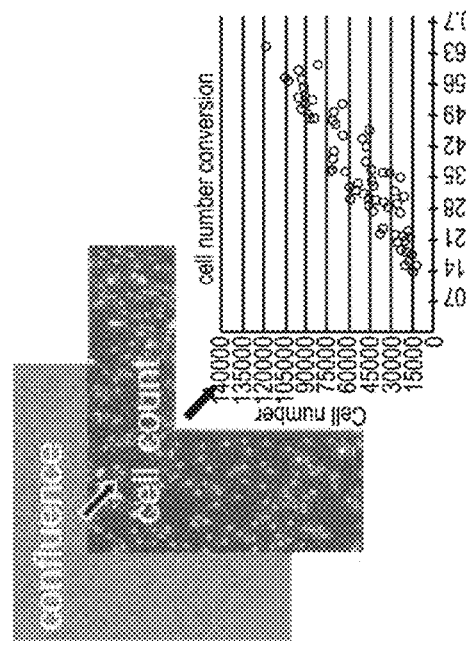

Automated Biopsy outgrowth tracking. Using the invention system, one can track the outgrowth of biopsies as well as other tissue sources by automated and traceable image analysis. As shown in FIGS. 6A-6C, images and growth rates are tracked during the production process.

In FIG. 6A, biopsies or discarded tissue are plated in multiple wells of a 6-well dish and maintained by an automated system that feeds, images, passages, and freezes fibroblast outgrowths. Examples of the image analysis interface is shown for a typical sample. A single plate is used per donated sample to minimize cross contamination. (FIG. 6B) Cell numbers are extrapolated from confluence measurements based on linear regression from a standard curve generated independently. (FIG. 6C) An example of cell counts for a typical biopsy outgrowth maintained on our automated system. Extrapolated cell numbers per patient sample are plotted for each well independently (top) allowing calculation of total output from the sample (bottom).

FIGS. 7A-7D shows FACS analyses and graphs showing automated iPSCreprogramming. Expression levels of pluripotent surface markers on reprogrammed human fibroblasts were followed over a 3 week period to observe reprogramming kinetics and determine optimal time points at which to isolate defined cell populations. (FIG. 7A) FACS gating scheme used for analysis. (FIG. 7B) A substantial proportion of cells co-expressing traditional pluripotency surface markers SSEA4 & TRA-1-60 retain the fibroblast marker CD13 at all timepoints during reprogramming using either retroviral or Sendai vectors to introduce reprogramming factors Oct4, Sox2, Klf4 and c-Myc. Box plots indicating aggregated data from 131 experiments (Retrovirus, n=66, Sendai virus, n=65) are shown. While Sendai mediated reprogramming produces more SSEA4/TRA-1-60 double positive cells (FIG. 7C), there is a delay in elimination of CD13 from the surface. (FIG. 7D) Example staining pattern of a patient cell line reprogrammed using Sendai/Cytotune system on our automated system. At both 7 and 13 dpi, more than half of SSEA4/TRA-1-60 double positive cells have lost CD13. Additionally, at both timepoints assayed, CD13 negative/Nanog positive cells are present in this fraction, suggesting these can be isolated by negative selection against CD13.

Figure 8B:
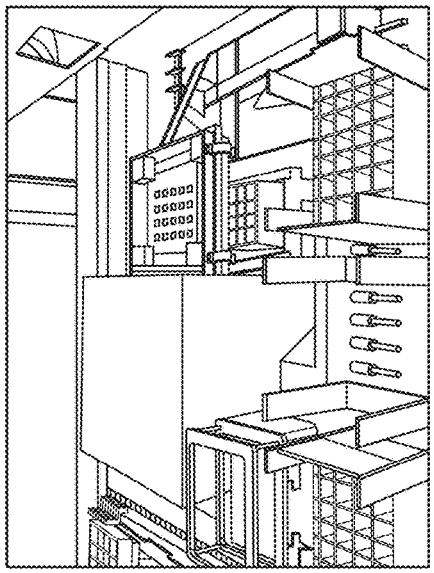
FIGS. 8A-8C show FACs pre-sort analyses and a part of the automated system to demonstrate enrichment and clone selection of iPSCs.
Figure 8C:
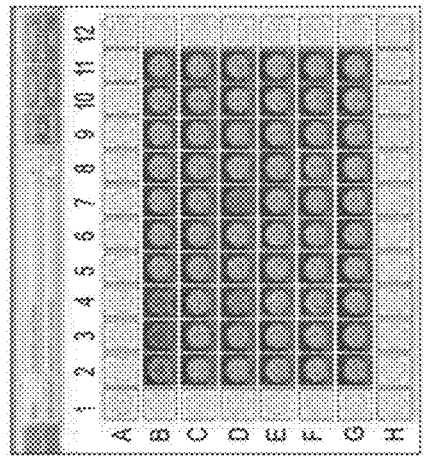
Figure 8A:
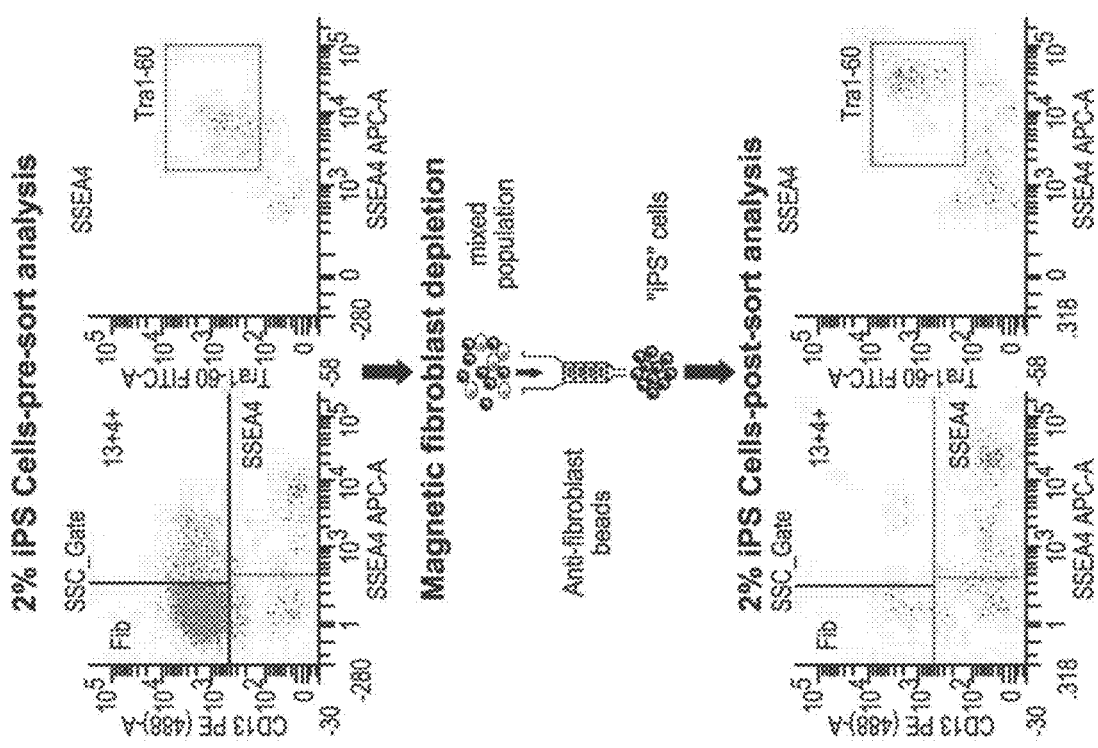

FIGS. 8A-8C shows FACs pre-sort analyses and a part of the automated system to demonstrate enrichment and clone selection of iPSCs. (FIG. 8A) Non-reprogrammed cell populations can be depleted from cultures of iPSCs by negative selection by a fibroblast marker. This strategy leaves iPSCs untouched. In the example, fibroblasts are efficiently removed from the culture containing 2% established iPSCs leaving TRA-1-60 positive iPSCs untouched. (FIG. 8B) A Miltenyi MultiMACS system integrated into Hamilton liquid handler can sort 24 samples in parallel. (FIG. 8C) An example colony of newly derived iPSCs derived by negative selection using anti-fibroblast antibody conjugated magnetic beads on the MultiMACS system. Phase contrast, nuclear stain by Sytox, surface marker stain by TRA-1-60 and nuclear Nanog staining (not shown). (FIG. 8D) The iPS enriched fraction from the anti-fibroblast magnetic negative selection step is plated on 96-well imaging plates at limiting dilution. These plates are screened using live-cell staining for the pluripotency surface marker TRA-1-60 or TRA-1-81. Wells with TRA-1-60 positive iPSCs are identified by automated image analysis using the Celigo software capable of single colony confirmation. Wells that meet both criteria of containing a single colony that is positive for the surface marker are selecting for passaging and expansion and QC. (FIG. 8E) (Not shown)—colonies produced by automated Sendai infection of adult fibroblasts.

iPS induction has also been demonstrated by automated transfection of modified mRNA. iPSC colonies from BJ fibroblasts were efficiently recovered after 10 days of automated delivery of a transfection mix containing modified mRNA. After an additional two days culture, the same well was stained with TRA-1-60 to identify undifferentiated cells. iPSCs in the well demonstrate that these are undifferentiated iPSCs. iPSC colonies isolated by purification away from non-reprogrammed cells using magnetic bead depletion on the automated system were efficiently recovered.

Figure 9B:
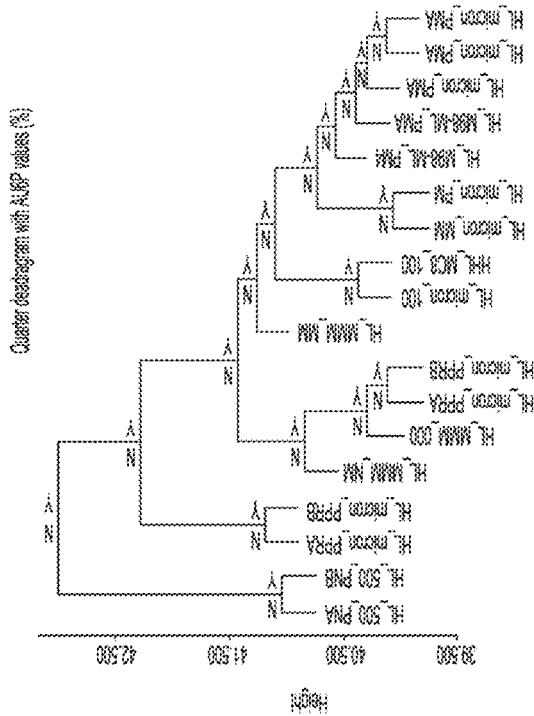
FIGS. 9A-9B provide an illustration for the scorecard assays described herein. The first stage of the quality control screen uses a panel of pluripotency differentiation and transgene markers to choose an initial set of three clones.
Figure 9A:
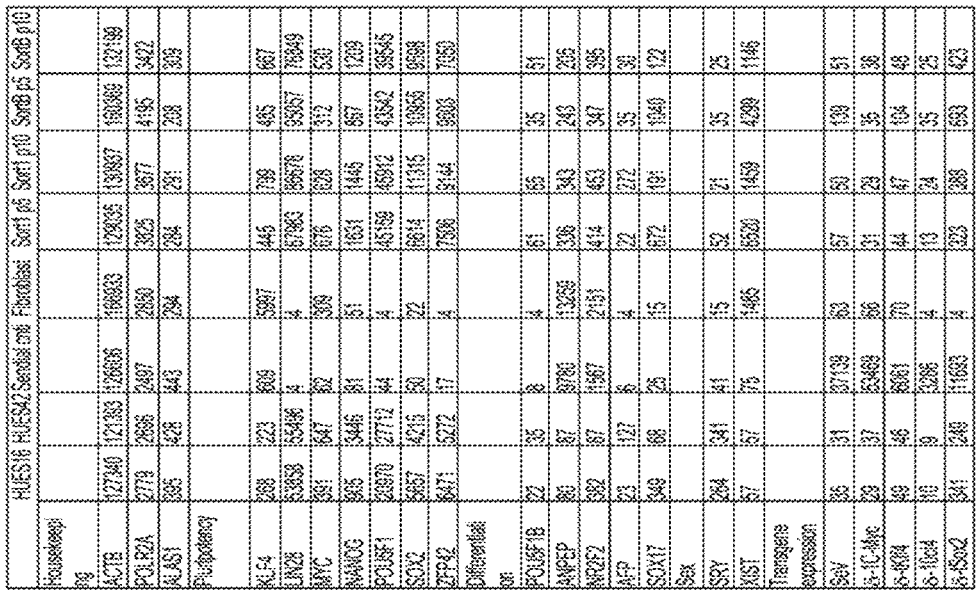

High throughput scorecard assays for gene expression have been generated. The first stage of our quality control screen uses a panel of pluripotency differentiation and transgene markers to choose an initial set of three clones. FIG. 9A shows transcript counts after normalization to HK gene expression for two HESC lines, Sendai positive control, fibroblast negative control, and iPS lines derived by FACS sorting assayed at passage 5 and 10. All assays are run relative to a panel of normal HESC and iPS lines maintained under similar conditions. Not shown was an example image of an Embryoid body generated on the system in 96-well V-bottom plates. The arrow points to the EB. FIG. 9C illustrates the second stage of our quality control screen uses an additional 83 germ layer/lineage markers to monitor differentiation capability in embryoid body assays. Single EBs are generated and pooled to generate RNA for expression analysis of germ layer markers in the embryoid body scorecard assay. Shown is a cluster dendrogram analysis of gene expression in EBs collected from nine different embryonic stem cells lines. After normalization, data generated from direct lysis of six EBs compares favorably to data generated from total RNA extracted and purified from EBs prepared from bulk culture.

Figures 10A, 10B:
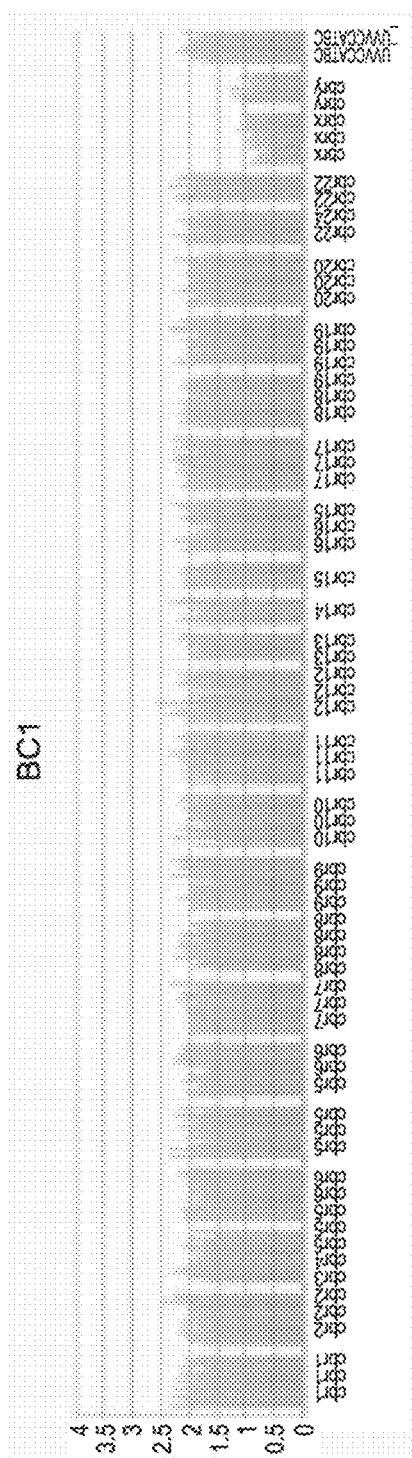
FIGS. 10A-10B demonstrate high throughput karyotyping of iPSCs based on Nanostring nCounter assays for CNVs.

FIGS. 10A-10B demonstrate high throughput karyotyping of iPSCs based on Nanostring nCounter assays for CNVs. FIG. 10A is an example of the nCounter Karyotype assay on BC1 iPSCs; FIG. 10B is an example of the nCounter Karyotype assay on 1016 fibroblasts with partial gain and loss of chromosome arms. Comparison to Affymetrix SNP 6.0 chip data demonstrating copy number gains on a portion of the q arm of Chr1 (top track, 1q21.2-1q43) and loss of part of the long arm of Chr6 (bottom track, 6q16.3-6q26). We have the ability to track the karyotype and identity of iPSCs in a high throughput assay based on Nanostring nCounter assays for CNVs. (FIG. 10A) Example of the nCounter Karyotype assay on BC1 iPSCs. (FIG. 10B) An example of the nCounter Karyotype assay on 1016 fibroblasts with partial gain and loss of chromosome arms. Comparison to Affymetrix SNP 6.0 chip data demonstrating copy number gains on a portion of the q arm of Chr1 (top track, 1q21.2-1q43) and loss of part of the long arm of Chr6 (bottom track, 6q16.3-6q26).

While preferred embodiments of the invention have been described, the invention is not limited to these embodiments, and the scope of the invention is defined by way of the appended claims.

What is claimed is:

1. An automated system for generating differentiated cells, comprising:
   (a) an automated cell plating unit configured for placing cells on a plate;
   (b) an automated induction unit configured for automated differentiation of cells by contacting the cells on the cell plating unit with differentiation factors to produce differentiated cells; and
   (c) an automated sorting unit configured for selectively sorting and isolating the differentiated cells produced by the induction unit by identifying markers specific to the differentiated cells, wherein the automated sorting unit is configured to simultaneously process multiple samples in parallel,
   wherein the automated system comprises controller software having functionality to control automation of the induction unit and the sorting unit.

2. The system of claim 1, further comprising:
   an expansion unit for expanding the isolated differentiated cells, and selecting the expanded differentiated cells.

3. The system of claim 1, further comprising:
   a freezing unit for freezing the isolated differentiated cells.

4. The system of claim 1, wherein the induction unit uses a viral vector to initiate differentiation.

5. The system of claim 4, wherein the induction unit uses a retrovirus or a Sendai virus to initiate differentiation.

6. The system of claim 1, wherein the induction unit uses small molecules, peptides, proteins or nucleic acids to initiate differentiation.

7. The system of claim 1, further comprising a cell banking unit for obtaining differentiated cells used by the plating unit.

8. The system of claim 7, wherein the cell banking unit comprises:
   a biopsy plating unit for placing biopsies on a plate;
   an outgrowth and passaging unit for growing cells; and
   a mycoplasma test unit for testing the presence of mycoplasma.

9. The system of claim 1, wherein the differentiated cells are selected from the group consisting of hematopoetic stem cells, muscle cells, cardiac muscle cells, liver cells, cartilage cells, epithelial cells, urinary tract cells, and neuronal cells.

* * * * *